(12) United States Patent
McKeon et al.

(10) Patent No.: US 8,273,047 B1
(45) Date of Patent: Sep. 25, 2012

(54) ADJUSTING AND APPLYING TRACTION TO A PATIENT'S ARM

(75) Inventors: Brian P. McKeon, Essex, MA (US);
Robert H. Bode, III, Topsfield, MA (US)

(73) Assignee: Perseus Athletic, LLC, Essex, MA (US)

( * ) Notice: Subject to any disclaimer, the term of this patent is extended or adjusted under 35 U.S.C. 154(b) by 459 days.

(21) Appl. No.: 12/622,065

(22) Filed: Nov. 19, 2009

Related U.S. Application Data

(60) Provisional application No. 61/116,192, filed on Nov. 19, 2008.

(51) Int. Cl.
*A61F 5/00* (2006.01)
(52) U.S. Cl. ............................................ 602/34; 602/32
(58) Field of Classification Search ............... 602/32–36, 602/38–40; 128/845, 877, 878, 879; 5/612, 5/623, 624, 646, 647, 648; 482/37, 92, 93, 482/97–103, 122, 124, 142; 135/123, 127; 114/39.29
See application file for complete search history.

(56) References Cited

U.S. PATENT DOCUMENTS

| | | | | |
|---|---|---|---|---|
| 2,633,124 A | * | 3/1953 | Yellin | 602/36 |
| 2,633,125 A | * | 3/1953 | Yellin | 602/36 |
| 3,167,068 A | * | 1/1965 | Carr | 602/32 |
| 5,003,967 A | * | 4/1991 | McConnell | 602/21 |
| 5,632,726 A | * | 5/1997 | Repice et al. | 602/36 |
| 5,676,158 A | * | 10/1997 | Katzman et al. | 128/845 |
| 5,704,881 A | * | 1/1998 | Dudley | 482/69 |
| 5,775,334 A | * | 7/1998 | Lamb et al. | 128/845 |
| 6,190,345 B1 | * | 2/2001 | Henderson | 602/32 |
| 7,857,779 B2 | * | 12/2010 | Gondringer | 602/33 |

* cited by examiner

*Primary Examiner* — Patricia Bianco
*Assistant Examiner* — Raymond E Harris
(74) *Attorney, Agent, or Firm* — Fish & Richardson P.C.

(57) ABSTRACT

A shoulder lift includes a hollow bent shaft that has a first end and a second end and that defines an interior of the bent shaft. First and second openings leading to the interior of the bent shaft are formed at the first and second ends, respectively. The shoulder lift also includes a cable having a first end and a second end. The cable runs through the first opening formed at the first end of the bent shaft and the second opening formed at the second end of the bent shaft such that the cable is threaded through the interior of the bent shaft. The first end of the cable is configured to be coupled to an arm sleeve for holding a patient's arm, and the second end of the cable is configured to be coupled to a support structure that locks into a to fixed position.

19 Claims, 22 Drawing Sheets

ADJUSTING AND APPLYING TRACTION TO A PATIENT'S ARM

CROSS REFERENCE TO RELATED APPLICATION

This application claims priority to U.S. Provisional Patent Application Ser. No. 61/116,192, filed on Nov. 19, 2008 and entitled "Systems and Methods for Adjusting and Applying Traction to a Patient's Arm," which is incorporated herein by reference in its entirety.

TECHNICAL FIELD

This disclosure relates to adjusting and applying traction to a patient's arm, for example, adjusting and applying traction to a patient's arm during shoulder surgery.

BACKGROUND

Certain shoulder surgeries (e.g., rotator cuff repairs and subacromial decompressions) may require that a patient's arm be physically held above the patient's body to allow the surgeon to see inside the patient's shoulder joint. During such a surgery, a shoulder lift may be used to lift the patient's arm above the patient's body and to allow the surgeon to adjust the angle of abduction, traction, and the forward flexion angle.

SUMMARY

An apparatus for adjusting and providing traction to a patient's arm during shoulder surgery is disclosed. The apparatus may allow a surgeon to change a patient's arm angle and the amount of traction applied to the arm during a surgical procedure. For example, the apparatus may hold the patient's arm still while allowing an orthopedic surgeon to adjust both the angle of abduction and the forward flexion angle with ease.

In one implementation, the arm of the patient is gripped in a sleeve that attaches to a cable that glides on an adjustable pulley along the inner side of a bent (e.g., semi-circular) boom. The angle of abduction of the patient's arm can be adjusted by moving the pulley to a different position along the boom. The far end of the cable connects to a spring scale that can be adjusted to achieve a desired level of traction on the patient's arm.

In another implementation, the arm of the patient is gripped in a sleeve that attaches to a cable that runs through the interior of a hollow, semi-circular telescoping boom. The angle of abduction of the patient's arm can be adjusted by increasing or decreasing the length of the telescoping boom. The far end of the cable connects to a spring scale that can be adjusted to achieve a desired level of traction on the patient's arm.

The shoulder lift assembly may attach to an operating table through a spring clamp having a locking mechanism that allows the lift to be connected or disconnected from the operating table relatively quickly and easily. The shoulder lift enables adjustments mid-surgery, simplifying the shoulder lift for surgeons and operating room technicians alike.

In one general aspect, a surgical shoulder lift includes a hollow, curved boom having a first end and a second end. The hollow, curved boom defines an interior of the curved boom, and a first opening that leads to the interior of the curved boom is formed at the first end of the curved boom while a second opening that leads to the interior of the curved boom is formed at the second end of the curved boom. A first pulley is mounted proximately to the first end of the curved boom and a second pulley is mounted proximately to the second end of the curved boom. In addition, the shoulder lift includes a mounting assembly configured to latch onto a rail of an operating table. The mounting assembly has a hollow columnar support that defines an interior of the columnar support that is configured to receive at least a portion of the second end of the curved boom in order to secure the curved boom within the columnar support. A tension slider ring also is wrapped around at least a portion of the circumference of the curved boom at a position along the curved boom that is between the first and second ends of the curved boom. The shoulder lift further includes a spring scale having a first end and a second end. The first end of the spring scale is coupled to the tension slider ring. The shoulder lift also includes a cable having a first end and a second end. The cable runs over the first pulley, through the first opening formed at the first end of the curved boom and the second opening formed at the second end of the curved boom such that the cable is threaded through the interior of the curved boom, and over the second pulley. The first end of the cable is configured to be coupled to an arm sleeve for holding a patient's arm and the second end of the cable is coupled to the second end of the spring scale. The spring scale is configured to measure the force with which the cable pulls on the second end of the spring scale.

Implementations may include one or more of the following features. For example, the hollow, curved boom may be a semi-circular boom, the hollow, curved boom may have an adjustable length, and/or the hollow, curved boom may be formed at least partially from a metal.

In some implementations, the hollow, curved boom may include a hollow, outer curved shaft that has a first end and a second end and a hollow, inner curved shaft that also has a first end and a second end. The hollow, outer curved shaft defines an interior of the hollow, outer curved shaft and a first opening leading to the interior of the outer curved shaft is formed at the first end of the outer curved shaft while a second opening leading to the interior of the outer curved shaft is formed at the second end of the outer curved shaft. Similarly, the hollow, inner curved shaft defines an interior of the hollow, inner curved shaft, and a first opening leading to the interior of the inner curved shall is formed at the first end of the inner curved shaft while a second opening leading to the interior of the inner curved shaft is formed at the second end of the inner curved shaft. In such implementations, the circumference of the outer curved shaft is greater than a circumference of the inner curved shaft, the first opening formed at the first end of the inner curved shaft forms the first opening at the first end of the curved boom, and the second opening formed at the second end of the outer curved shaft forms the second opening at the second end of the curved boom. Furthermore, the first opening at the first end of the outer curved shaft is configured to receive the second end of the inner curved shaft such that the length of the curved boom can be adjusted by sliding the inner curved shaft into and out of the outer curved shaft. The shoulder lift also may include a means for locking the inner curved shall in a fixed position within the outer curved shaft.

In some implementations, the tension slider ring may be configured to slide along the curved boom. For example, the tension slider ring may be configured to increase tension in the cable by sliding the tension slider ring along the curved boom away from the second end of the curved boom and toward the first end of the curved boom. In contrast, the tension slider ring may be configured to decrease tension in the cable by sliding the tension slider ring along the curved boom towards the second end of the curved boom and away from the first end of the curved boom. In addition, the shoulder lift also may include a means for locking the tension slider ring in a fixed position along the curved boom. In some implementations, the tension slider ring may include a collar that is configured to be wrapped around at least a portion of the circumference of the curved boom and that is formed at least partially from a metal. Additionally or alternatively, the tension slider ring may include a fabric strap that has a hook and loop fastening mechanism and that is configured to be wrapped around the circumference of the curved boom and fastened to itself using the hook and loop fastening mechanism.

The mounting assembly configured to latch onto a rail of an operating table may include a clamp configured to clamp onto a rail of an operating table. Furthermore, the second end of the curved boom may be press-fit into the interior of the columnar support of the mounting assembly. In some implementations, the hollow columnar support of the mounting assembly may be configured to enable the curved boom to rotate within the interior of the hollow columnar support. Additionally or alternatively, the shoulder lift also may include a means for locking the curved boom into a fixed position within the interior of the hollow columnar support such that rotation of the curved boom within the interior of the hollow columnar support is prevented.

In some implementations, the mounting assembly of the shoulder lift may include a rotatable plate, and the hollow columnar support may be mounted on the rotatable plate such that the hollow columnar support rotates when the rotatable plate rotates. In such implementations, the curved boom may be secured within the interior of the hollow columnar support such that the curved boom and the hollow columnar support rotate together when the rotatable plate rotates. In such implementations, the shoulder lift also may include a means for locking the rotatable plate in a fixed position from which rotation is prevented.

In another general aspect, a surgical shoulder lift includes a hollow, curved boom having a first end and a second end. The hollow, curved boom defines an interior of the curved boom, and a first opening that leads to the interior of the curved boom is formed at the first end of the curved boom while a second opening that leads to the interior of the curved boom is formed at the second end of the curved boom. A first pulley is mounted proximately to the first end of the curved boom and a second pulley is mounted proximately to the second end of the curved boom. In addition, a tension slider ring is wrapped around at least a portion of the circumference of the curved boom at a position along the curved boom that is between the first and second ends of the curved boom. The shoulder lift further includes a spring scale having a first end and a second end. The first end of the spring scale is coupled to the tension slider ring. The shoulder lift also includes a cable having a first end and a second end. The cable runs over the first pulley, through the first opening formed at the first end of the curved boom and the second opening formed at the second end of the curved boom such that the cable is threaded through the interior of the curved boom, and over the second pulley. The first end of the cable is configured to be coupled to an arm sleeve for holding a patient's arm and the second end of the cable is coupled to the second end of the spring scale. The spring scale is configured to measure the force with which the cable pulls on the second end of the spring scale.

In yet another general aspect, a surgical shoulder lift includes a hollow bent shaft having a first end and a second end. The hollow, bent shall defines an interior of the bent shaft, and a first opening leading to the interior of the bent shaft is formed at the first end of the bent shaft while a second opening leading to the interior of the bent shaft is formed at the second end of the bent shaft. In addition, the surgical shoulder lift also includes a cable having a first end and a second end. The cable runs through the first opening formed at the first end of the bent shaft and the second opening formed at the second end of the bent shaft such that the cable is threaded through the interior of the bent shaft. The first end of the cable is configured to be coupled to an arm sleeve for holding a patient's arm, and the second end of the cable is configured to be coupled to a support structure that locks into a fixed position so as to provide tension in the cable when the first end of the cable is coupled to an arm sleeve, holding a patient's arm.

The details of one or more implementations are set forth in the accompanying drawings and the description below. Other features will be apparent from the description and drawings, and from the claims.

DETAILED DESCRIPTION

Figure 1:
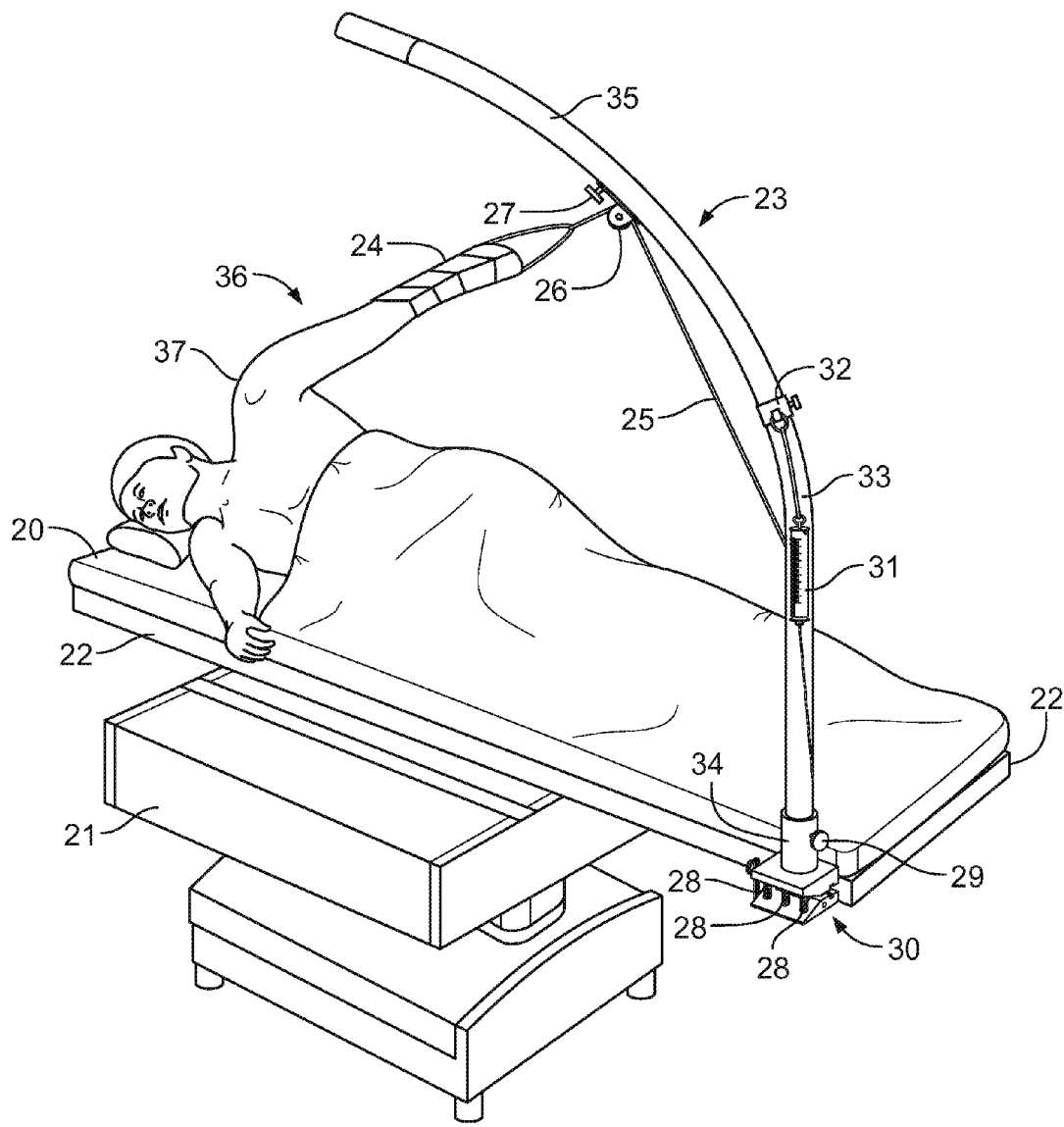
FIG. 1 is a perspective view of an example of a shoulder lift demonstrating use of the shoulder lift to hold a patient's arm above the patient's body.

In one implementation, a shoulder lift attaches to an operating table and has a single bent (e.g., semicircular) tubular support. A cable is run along the bent support and over an adjustable pulley. One end of the cable connects to a sleeve that holds a patient's arm during surgery. The other end of the cable, once run over the pulley and along the bent support, connects to a spring traction scale. The spring traction scale also is connected to a slider, which slides along the outside of the bent support, enabling the force exerted on the cable to be varied by sliding the slider to different positions along the bent support. The spring traction scale attaches to the slider by a hook; making any adjustment to the position of the slider, and thus the force exerted on the cable, fast and simple. The spring traction scale may be configured to measure a range of force that can be exerted on the cable, for example, ranging from 0 to 20 pounds of force.

The shoulder lift is supported by a clamp at the base of the bent tubular support. In some implementations, the clamp is a spring clamp that has a fitted slot to engage a rail on the side of an operating table. In such implementations, spring(s) in the rear of the clamp provide a force which closes the clamp onto the rail, and the clamp may be configured such that only one hand is required to squeeze it for it to be opened to be placed on the rail. The clamp may include a knob for locking the clamp in place after the clamp has been secured in a lateral position on the rail. For example, the locking knob may slide through a slot and screw into the side of the clamp, locking the apparatus to the operating table.

Atop the clamp, a hollow tube is configured to hold and receive the bent tubular support. The tube is structured to enable the shoulder lift to rotate freely within the tube and, in some implementations, up to 360 degrees, allowing the surgeon to achieve any forward flexion angle desired. Once the appropriate angle is attained, the shoulder lift can be locked into position by turning a knob on the outside of the hollow tube. By turning the knob, the shoulder lift may be locked into position by a screw that applies pressure against the shoulder lift. When a new forward flexion angle is desired, the surgeon or person adjusting the lift may turn the knob to release the pressure against the shoulder lift allowing the shoulder lift to be rotated freely again.

A slot is cut out along the inside of the bent tubular support to allow a pulley to slide along the bent tubular support. By turning a knob, the pulley can be either locked in place or unlocked to move freely along the slot. This pulley, over which the cable runs, can be slid along the slot to any desired arm angle (e.g., from approximately 20 degrees to 90 degrees). Once the desired angle of abduction is attained, the knob can be turned to lock the pulley in place with the arm at the desired angle.

The shoulder lift allows a surgeon to maneuver a patient's arm to a desired position with a desired amount of traction. As such, the shoulder lift may be suitable for different surgeons who prefer different arm angles/positions during surgery. For example, the shoulder lift may be suitable for surgeons who prefer a steep angle of abduction as well as for surgeons who prefer a shallow angle of abduction.

Implementations of shoulder lifts are now described in more detail with reference to FIGS. 1-19.

Figure 3:
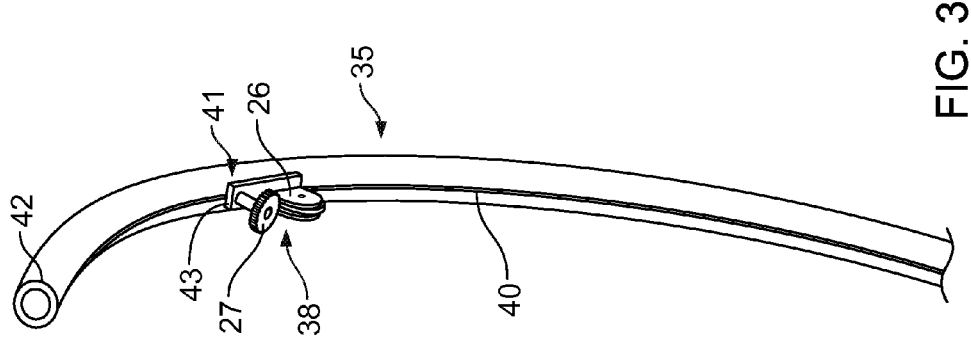
FIGS. 2-3 are perspective views of the shoulder lift of FIG. 1.
Figure 2:
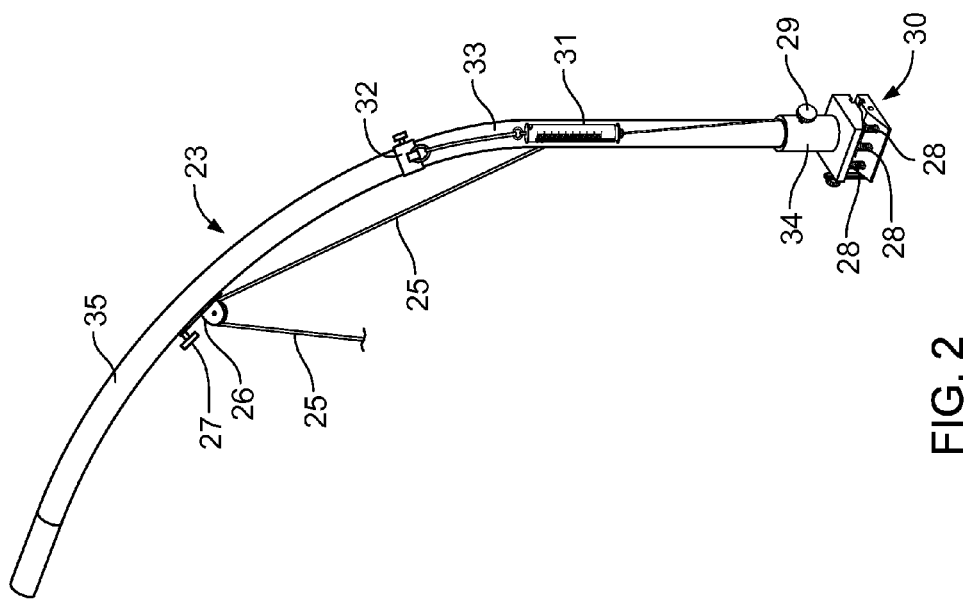

Referring to FIGS. 1-3, there is shown a first example of a shoulder lift 23 for holding a patient's arm 36 above the patient's body during shoulder surgery. The shoulder lift 23 is attached to the operating table 20 with the patient lying on his/her side during the surgical procedure. The table has two rails 22 on opposite sides to which surgical equipment can be attached and held during surgical procedures. The shoulder lift 23 is attached to one of these rails 22, depending upon on which shoulder 37 the operation is being performed. For example, if the patient's left shoulder is the shoulder on which the operation is being performed, the shoulder lift 23 may be attached to the rail 22 on the patient's ride side. Similarly, if the patient's right shoulder is the shoulder on which the operation is being performed, the shoulder lift 23 may be attached to the rail 22 on the patient's left side.

The shoulder lift 23 includes a system cable 25, a bent cylindrical shaft 35, an adjustable pulley system (e.g., angle of abduction pulley system) 38 over which the system cable 25 runs, a spring clamp 30, a forward flexion attachment 34 that supports the bent cylindrical shaft 35, a tension slider ring 32, and a linear spring scale 31. The shoulder lift 23 may be configured to prevent any undesired movement of the arm during the surgical procedure. In this regard, the shoulder lift 23 may enable a surgeon to place a patient's arm 36 in a desired position and maintain this position until a new arm position is desired.

As seen in FIG. 2, the bent cylindrical shaft 35 supports an arm through the system cable 25. The arm is wrapped in the arm sleeve 24 which connects to a first end of the system cable 25. The cable 25 runs over the pulley 38 and then down towards the forward flexion attachment 34 that secures the bent cylindrical shaft 35 to the clamp 30. A second pulley (not shown) is mounted at a position along the length of the bent cylindrical shaft 35. The cable 25 runs over this second pulley and loops back upward again along the bent cylindrical shaft 35, where the second end of the cable 25 is attached to one end of the linear spring scale 31. A second end of the linear spring scale 31 is connected to a tension slider ring 32, and the tension slider ring 32 is configured to be able to slide along the bent tubular shall 35 and to be locked into a desired position along the bent tubular shaft 35. By sliding the tension slider ring 32 up and down the bent tubular shaft 35, the tension in the cable 25 can be adjusted, thereby enabling the traction applied to the patient's arm 36 to be varied. For example, sliding the tension slider ring 32 up the bent tubular shaft 35 increases the tension in the cable 25 thereby reducing the traction applied to the patient's arm 36. Similarly, sliding the tension slider ring 32 down the bent tubular shaft 35 decreases the tension in the cable 25 thereby reducing the traction applied to the patient's arm 36. Meanwhile, the linear spring scale 31 measures the force being exerted on the patient's arm 36 via the tension in the cable 25, thereby providing the surgeon or the operating room technician with quantifiable measure of the traction being applied to the patient's arm 36.

The shaft 35 may be made from a light weight, strong metal that also withstands corrosion from cleaning agents, such as, for example, aluminum or titanium. An angle of abduction slot 40 is formed along the interior of the bent shaft 35 enabling the cable 25 to run through the bent shall 35 and the pulley 38 to slide along the bent shaft 35 such that the angle of abduction of the patient's arm can be changed.

Referring to FIG. 3, the slot 40 may extend the full length of the bent shaft 35, from the top of the shaft 35 to the bottom of the shaft 35, which is received within the forward flexion attachment 34. Alternatively, the slot 40 may extend only along a limited portion of the bent shaft 35. The angle of abduction slot 40 allows a pulley mount 26 to slide within the slot and lock into place with the tightening of the angle of abduction knob 27. The pulley mechanism may allow the angle of abduction to be changed relatively easily.

Figure 4A:
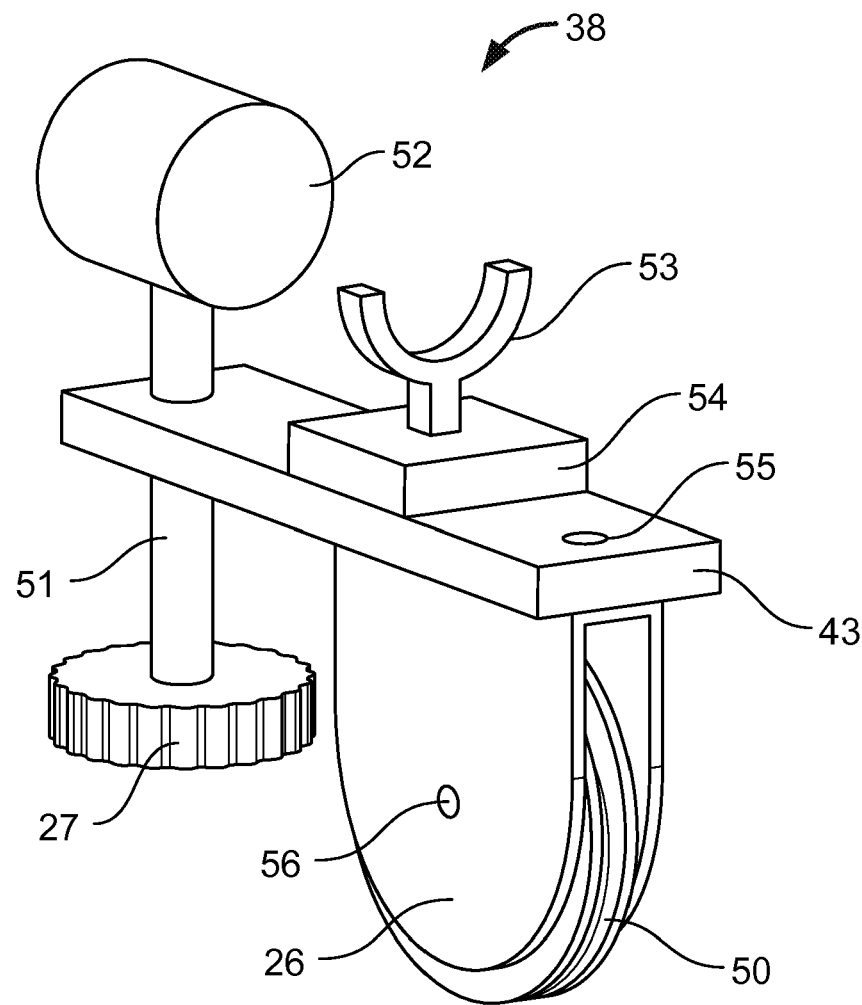
FIGS. 4A and 4B show perspective and exploded perspective views, respectively, of an example of a pulley system for use in a shoulder lift.
Figure 4B:
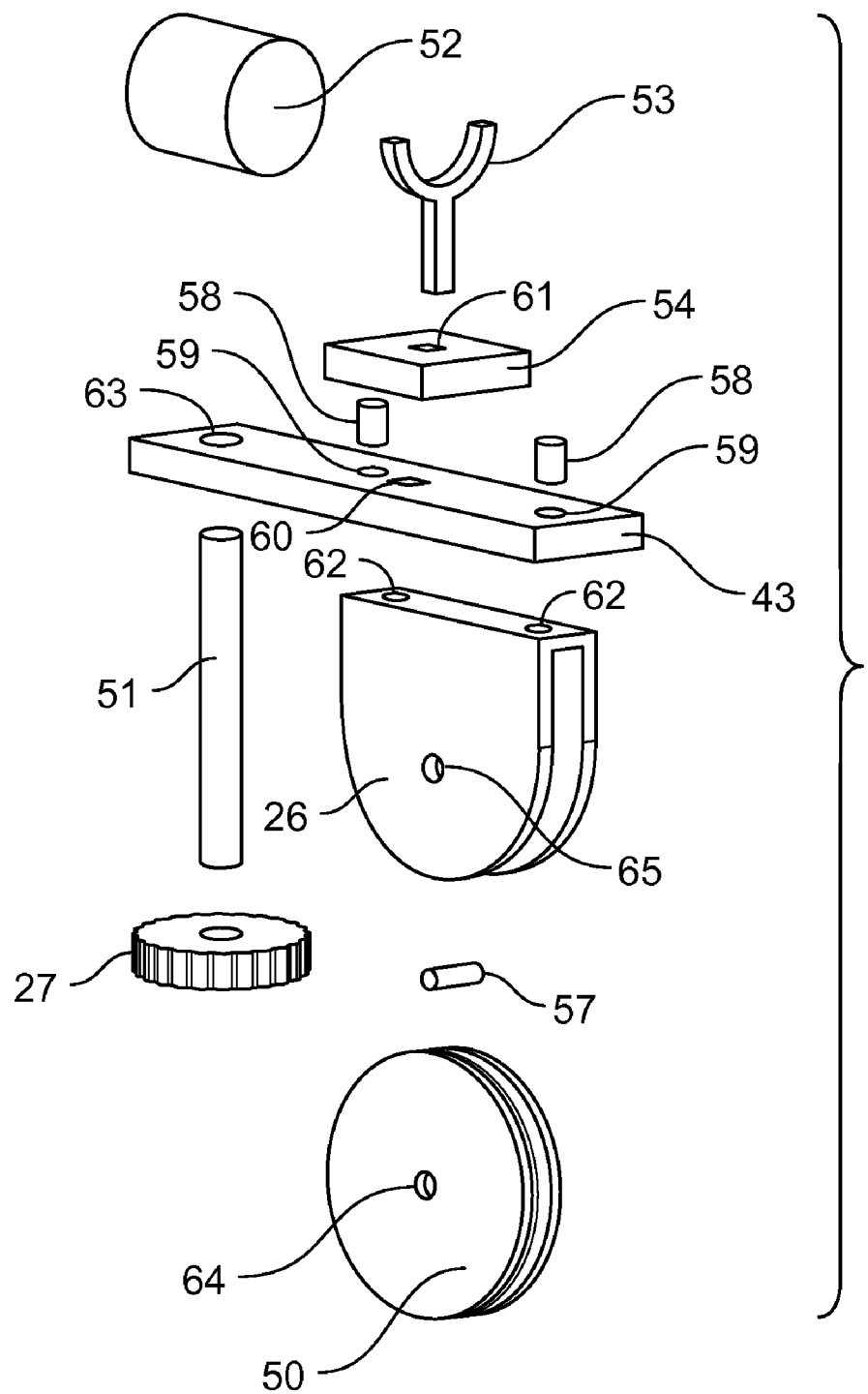
Figure 5A:
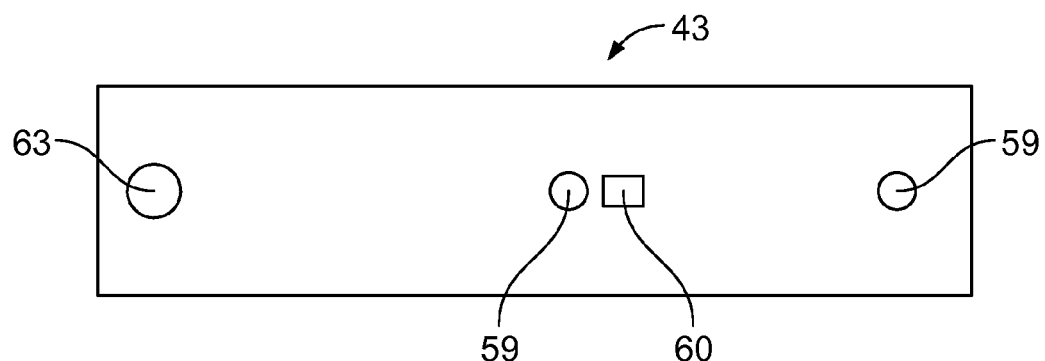
FIGS. 5A and 5B are top views of examples of lower and upper platforms on which the pulley system of FIGS. 4A and 4B may be mounted.
Figure 5B:
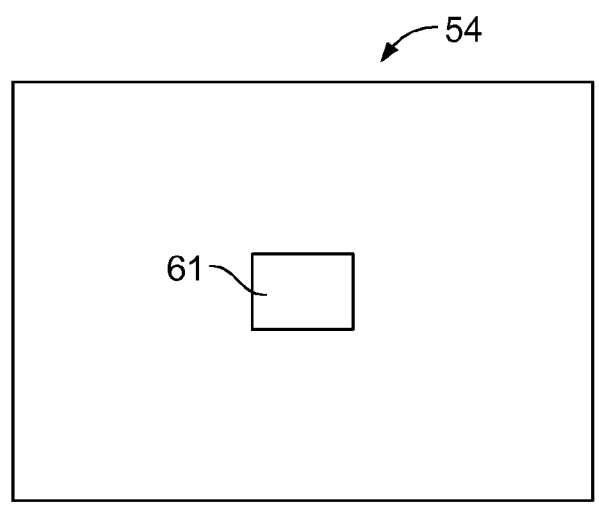

FIG. 4A is a view of the angle of abduction pulley system 38. The pulley system 38, seen in an exploded view in FIG. 4B, may be made from a metal that withstands corrosion from cleaning agents and may be mounted to a flat platform 43 (seen in FIG. 5A) by pulley mounting screws 58 which screw into the angle of abduction mounting holes 59 formed in platform 43. At the end of platform 43, a hole 63 is formed through which the angle of abduction knob 27 and angle of abduction shaft 51 rotate to tighten the pulley system in a location along the angle of abduction slot 40 in the bent tubular support. This lower platform 43 may be welded or otherwise fastened (e.g., screwed) to an upper platform 54

(seen in FIG. 5B), which maintains a separation distance so as to prevent the pulley 38 from interfering with the adjustment. The slot 40 is configured to receive the angle of abduction slider 53, which allows the pulley 38 to slide freely in the slot 40. The thickness of the angle of abduction slider 53 may be less than that of the angle of abduction slot 40 so as to allow the entire angle of abduction pulley system 38 to be disconnected from the shoulder lift 23 if desired, for example, for cleaning or maintenance purposes.

Figure 6:
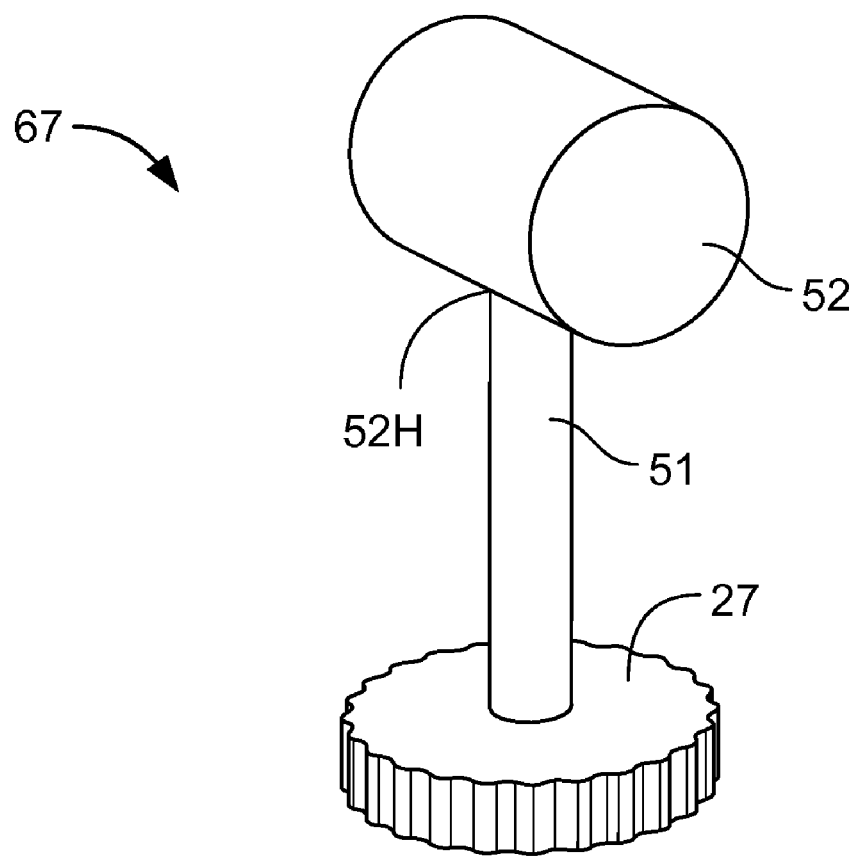
FIG. 6 is a perspective view of an example of a tightening mechanism for the pulley system of FIGS. 4A and 4B.

The pulley 38 may be locked into position through the tightening of the angle of abduction knob 27, which screws into the angle of abduction pulley lock 52 (seen in more detail in FIG. 6). A hole 52H is formed in the angle of abduction pulley lock 52 and configured to enable the angle of abduction shaft 51 to be screwed into it. This shaft is prevented from rotating by the bent cylindrical shaft 35, and thus provides a mechanism that can tighten and lock the angle of abduction pulley system 38 in place.

Figure 7:
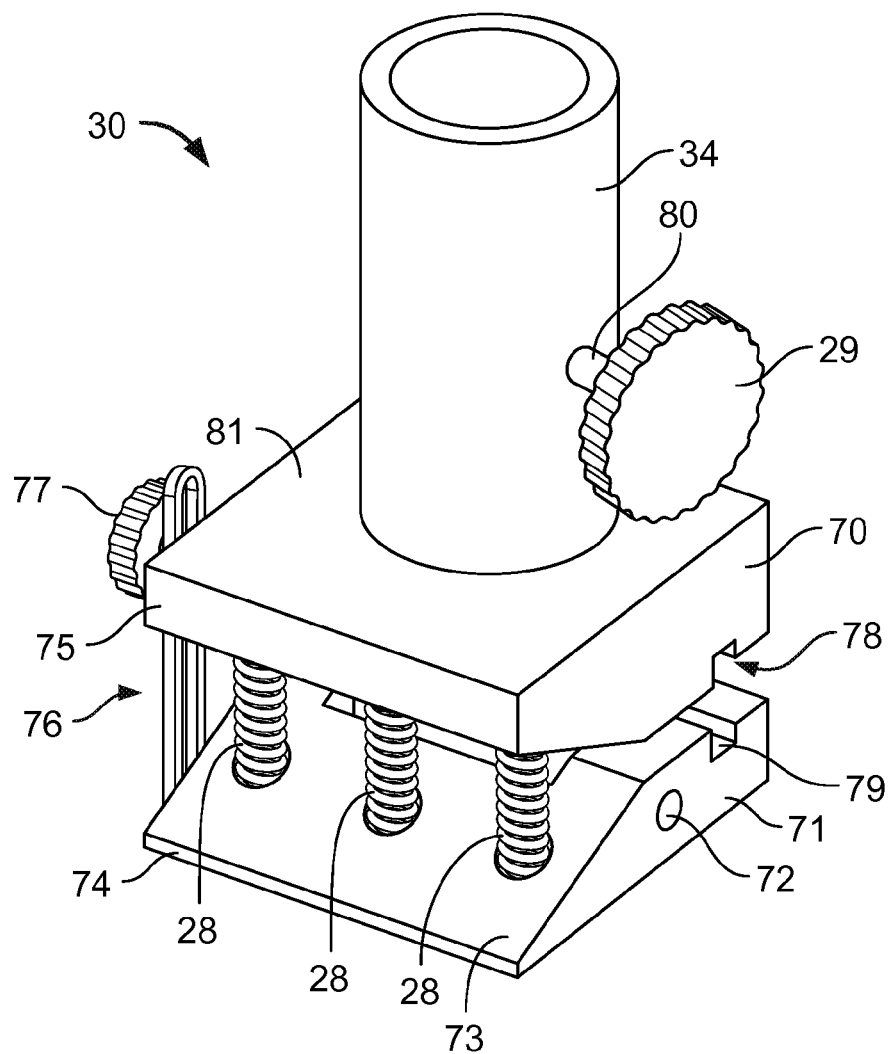
FIG. 7 is a perspective view of an example of a spring clamp for attaching a shoulder lift to an operating table.
Figure 8:
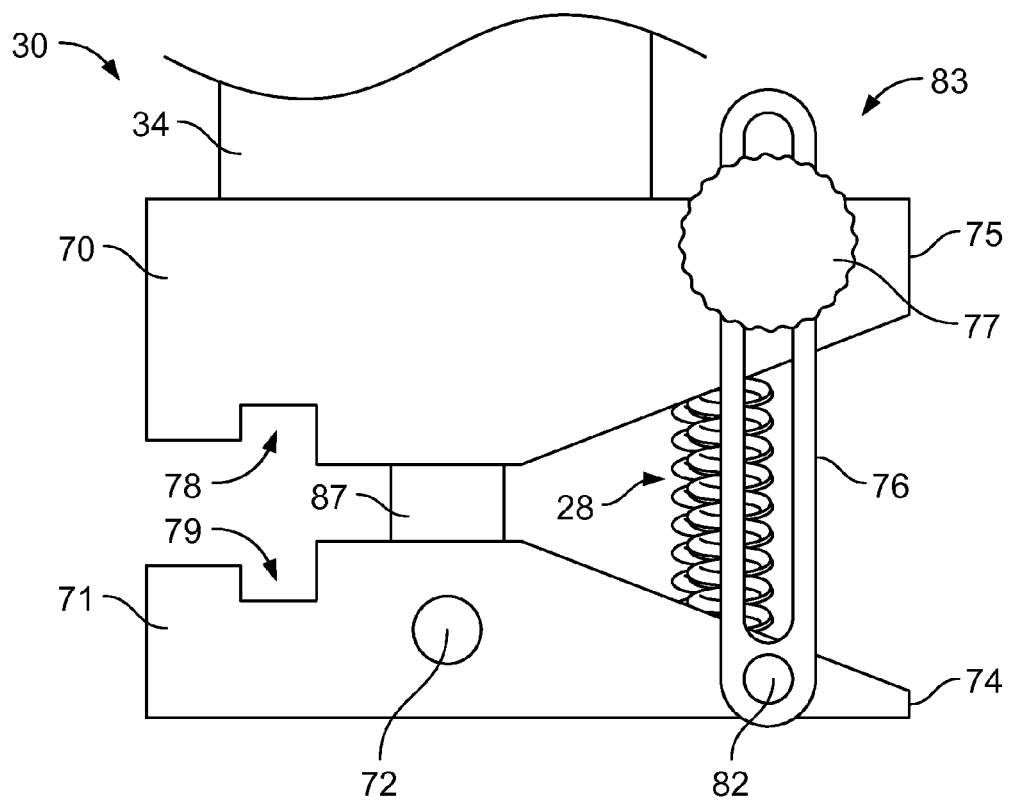
FIG. 8 is a side view of the spring clamp of FIG. 7.
Figure 9A:
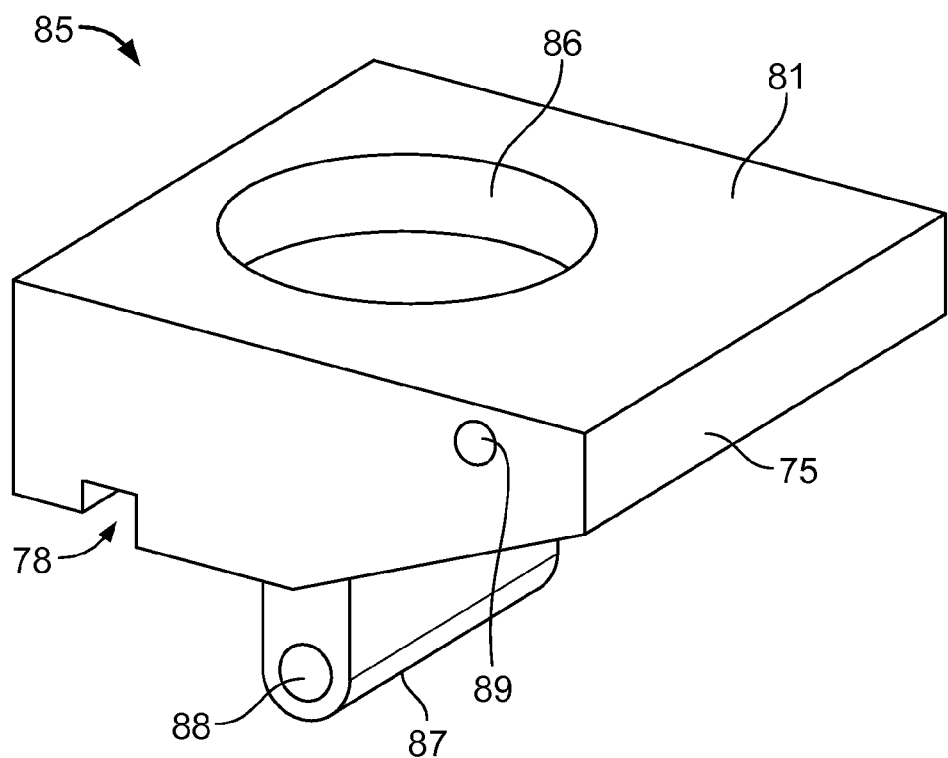
FIGS. 9A and 9B are perspective views of the upper and lower halves of the spring clamp of FIG. 7.
Figure 9B:
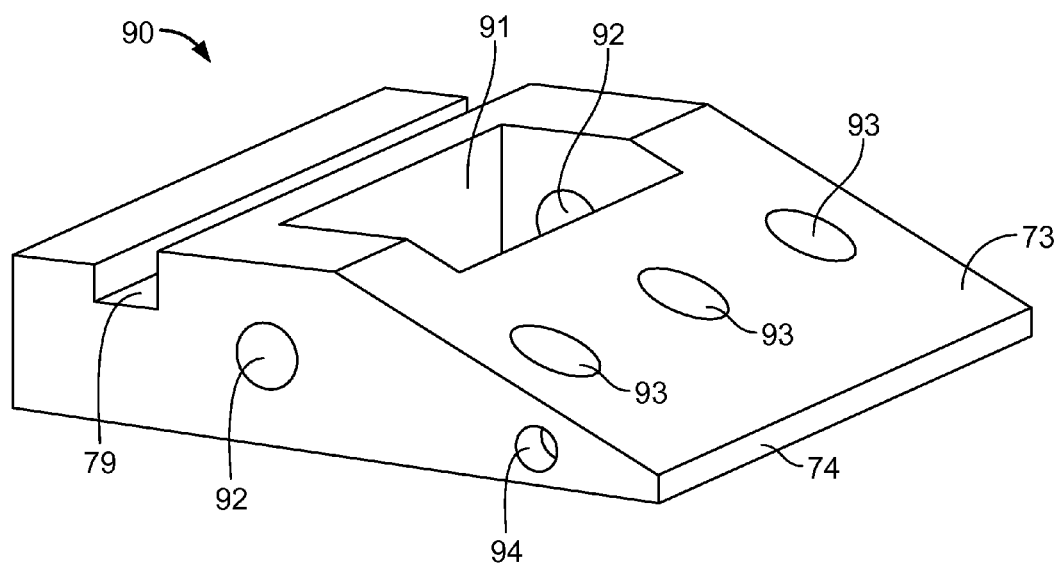
Figure 10:
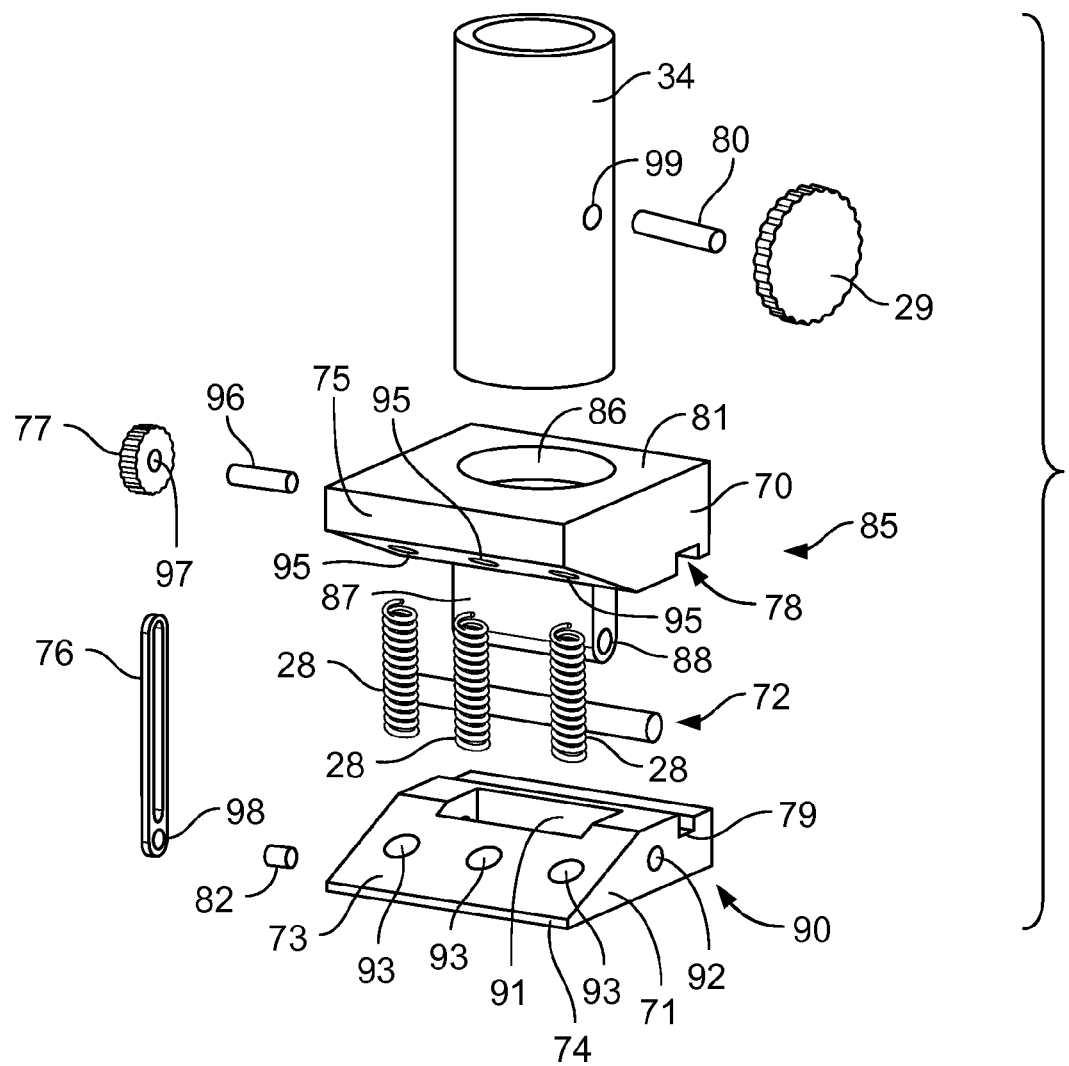
FIG. 10 is an exploded view of the spring clamp of FIG. 7.
Figure 11:
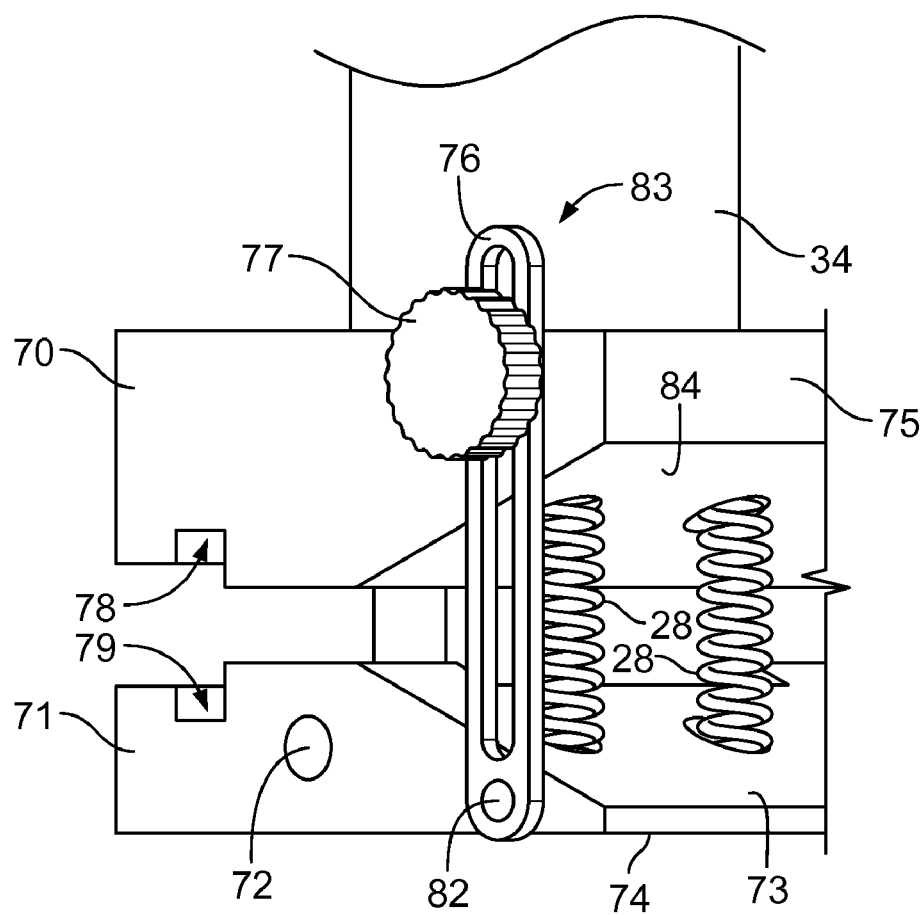
FIG. 11 is a view of an example of a locking mechanism for use in the spring clamp of FIG. 7.

FIGS. 7 and 8 show different views of an example of a spring clamp 30 that is configured to attach a shoulder lift, such as, for example, shoulder lift 23, to the operating table 20. The spring clamp 30 may allow for quick and easy attachment of the shoulder lift 23. The spring clamp 30 may be constructed of a strong and durable metal, one that is non-corrosive from cleaning agents. In addition, the spring clamp 30 may be constructed from two specifically cut metal blocks. In such implementations, the two halves may be secured together by a pin 72 about which the two halves can rotate relative to each other. FIGS. 9A and 9B show the two halves from which the spring clamp 30 is constructed separately, with FIG. 10 showing an exploded view of the entire clamp 30.

FIG. 9A illustrates the upper half 85 of the clamp 30. A hole (the forward flexion attachment slot) 86 is formed in the top of the upper half 85 of the clamp 30 and is configured to receive the forward flexion attachment 34. This assembly enables the bent tubular shaft to be inserted and connected to the clamp 30. Extruding from the bottom of the upper clamp is an extended piece (the upper clamp extrusion) 87 within which clamp pin slot 88 is formed. This pin slot 88 is cut through the entire upper clamp extrusion 87 allowing a pin to fit through the slot and join the two halves 85 and 90 of the clamp 30. A specifically sized slot (the upper rail slot) 78 is also cut through the front half of the upper clamp 85. The dimensions of this slot 78 are configured to fit around the upper end of the operating table rail 22. The rear of the upper clamp 85 has a sloped face 84 within which three holes 95 are formed for engaging compression springs 28.

FIG. 9B shows the lower clamp 90. The upper half 85 and the lower half 90 are configured to mate together to form the clamp assembly 30. Toward the middle of the lower clamp 90, a slot (the clamp mating slot) 91 is formed in the lower clamp 90. This slot 91 is configured to receive and mate with the upper clamp extrusion 87. In addition, clamp pin holes 92 are formed in the walls defining slot 91. These holes are configured to allow a pin to be press-fitted through the pin holes as well as the clamp pin slot 88 of the upper clamp extrusion 87 thereby providing a hinge about which the upper 85 and lower 90 halves can rotate. Toward the front end of the lower clamp 90, a specifically sized gap (the lower rail slot) 79 is cut through the top surface of the lower claim 90. The dimensions of this slot 79 are configured to fit around the lower end of the operating table rail 22. The rear of the lower clamp 90 has a lower sloped face 73 that is substantially the same size as the sloped face 84 of the upper clamp 85 and within which three spring holes 93 are formed that are configured to receive the compression springs 28. The upper spring holes 95 may match the lower spring holes 93 to enable easy placement of the compression springs 28.

The spring clamp 30 provides two established rail slots 78 and 79 within which the operating table rail 22 fits. With three possible spring holes 93 and 95 for compression springs 28, the clamp 30 stays pressured against the rail 22 and enables a well secured connection. The clamp 30 also contains a locking mechanism 83 (seen in more detail in FIGS. 8 and 11).

Clamp lock 76 enables the clamp to be fully opened and closed without hindrance. The clamp 30 can be locked by tightening the clamp knob 77 on the side of the clamp 30. The clamp knob 77 turns the clamp locking shaft 96 which screws into a screw hole formed in the top half of the clamp 30. The clamp knob 77 thus is able to exert pressure against the clamp lock 76 hence locking the clamp 30 in position.

Figure 12A:
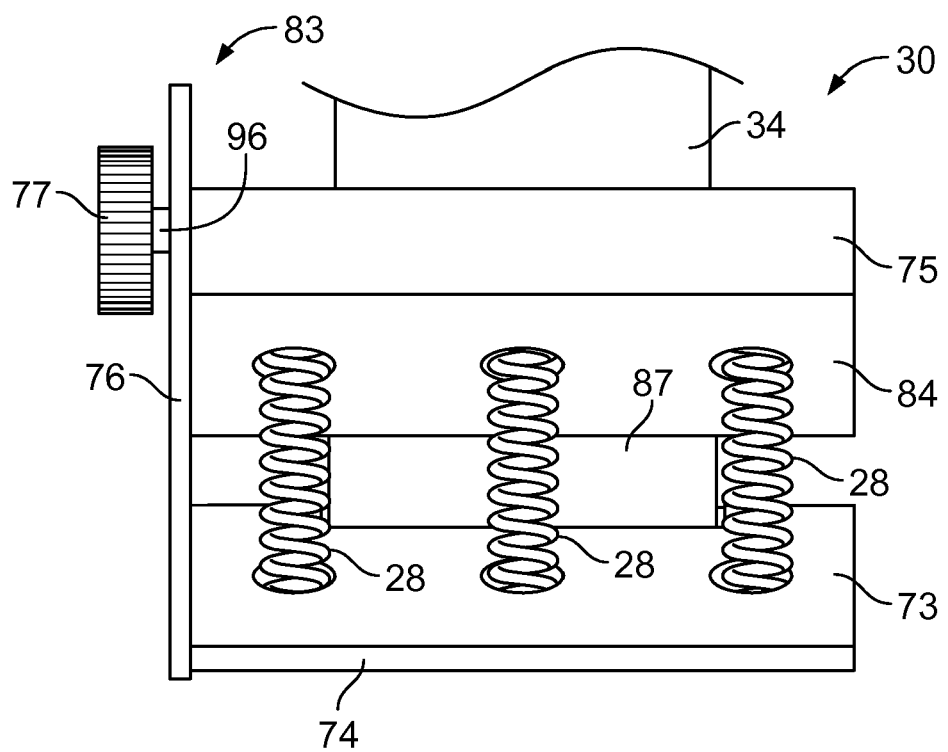
FIGS. 12A and 12B are rear views of the back end of the spring clamp of FIG. 7.
Figure 12B:
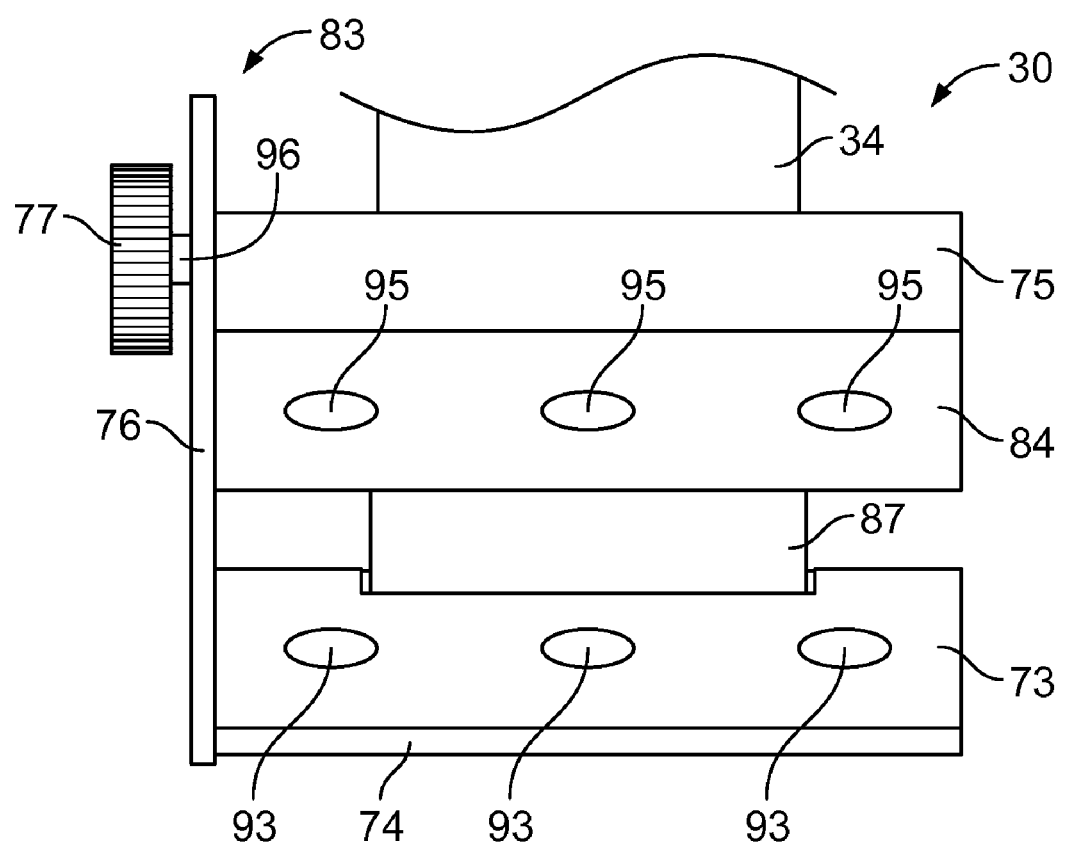

The springs 28 of the spring clamp 30 are better seen in FIGS. 12A and 12B. These rear views illustrate examples of locations for the compression springs 28. There are matching slots 93 and 95 in the upper and lower sloped faces 84 and 73 of the clamp 30. FIG. 12A shows the rear of the clamp 30 without the springs 28 inserted into the spring holes 93 and 95 while FIG. 12B shows the same view with the springs 28 in the spring holes 93 and 95.

Figure 13A:
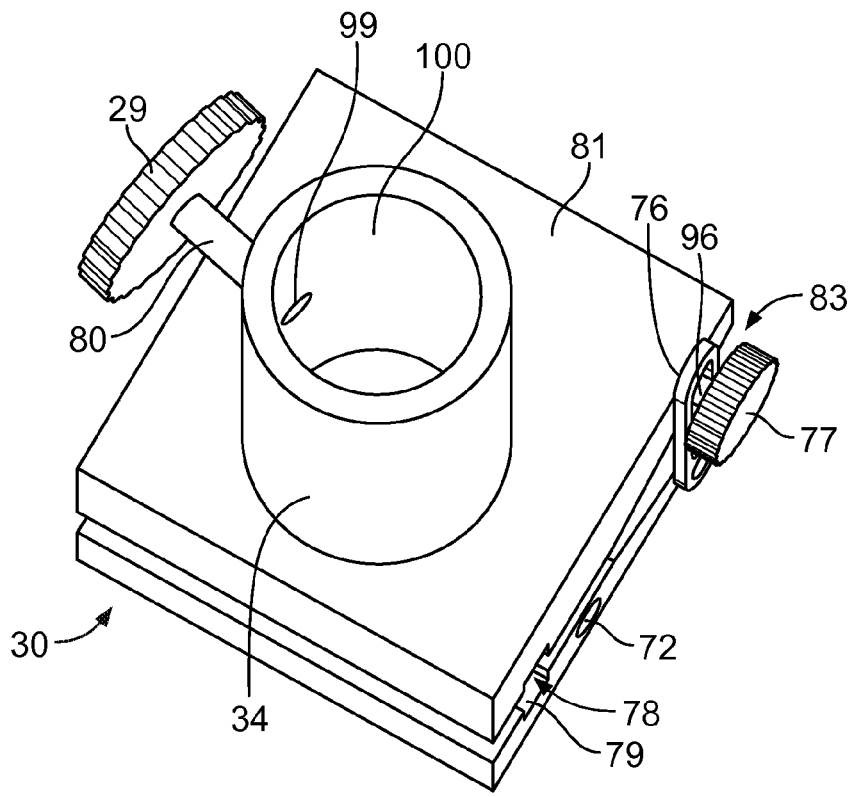
FIGS. 13A and 13B are perspective views of an example of an assembly for mounting a shoulder lift to an operating table.
Figure 13B:
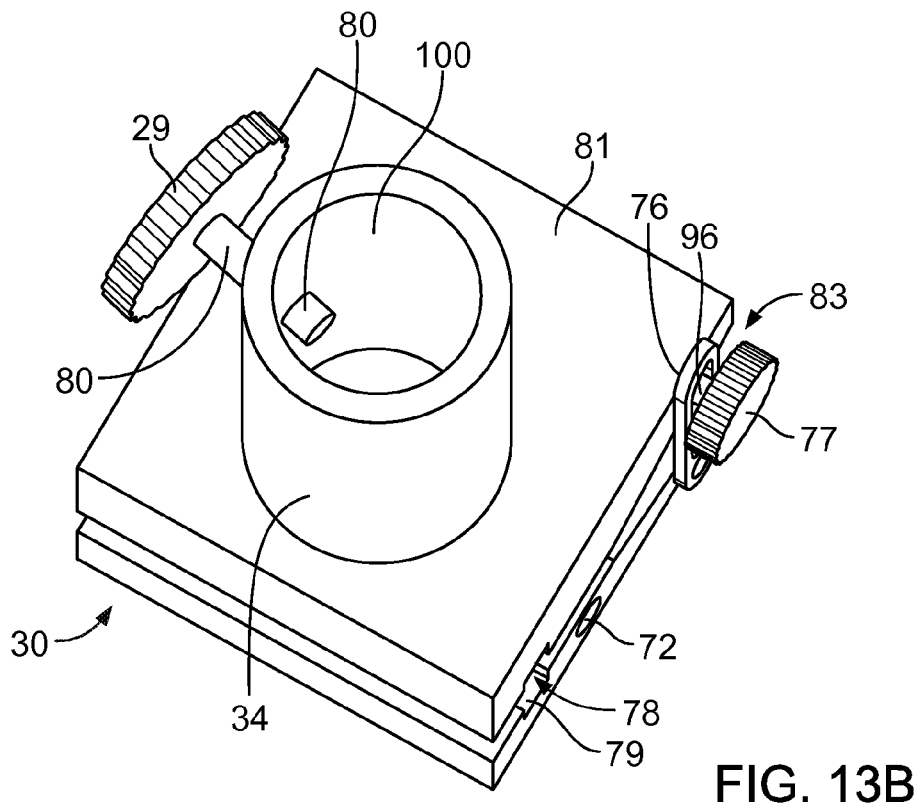
Figure 14:
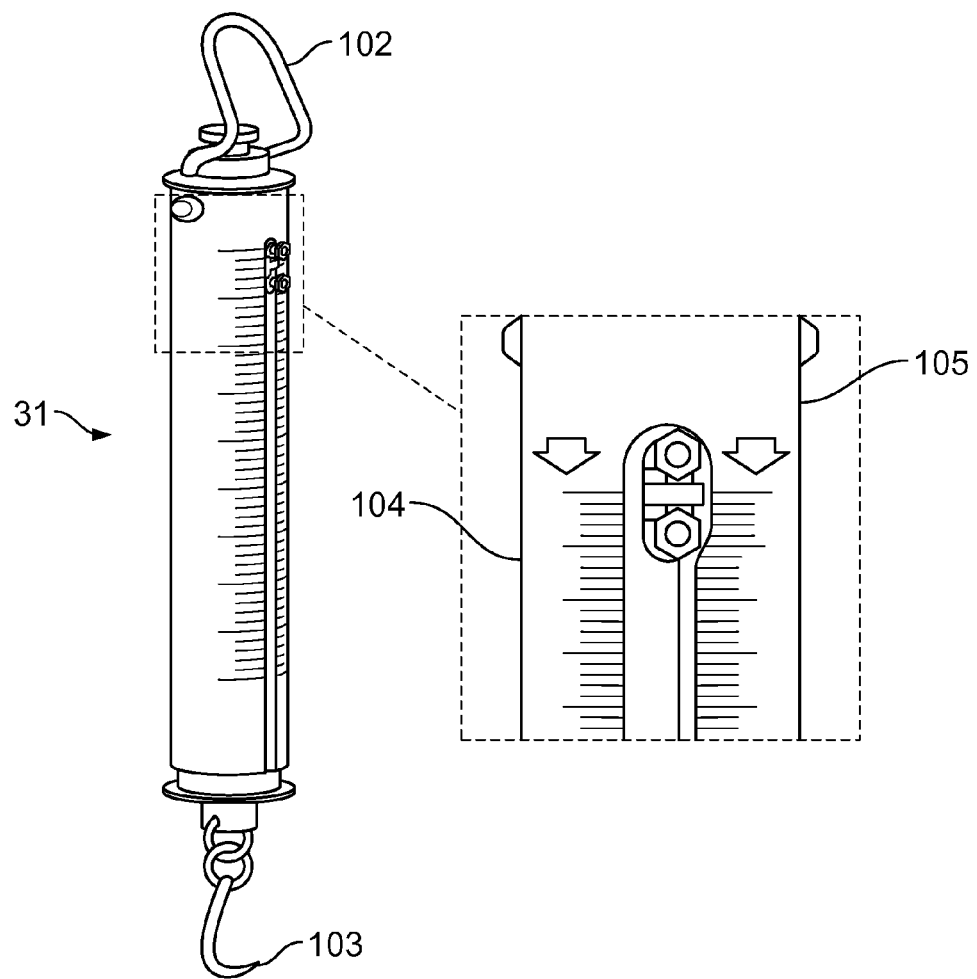
FIG. 14 is an example of a spring scale for use in a shoulder lift.
Figure 15:
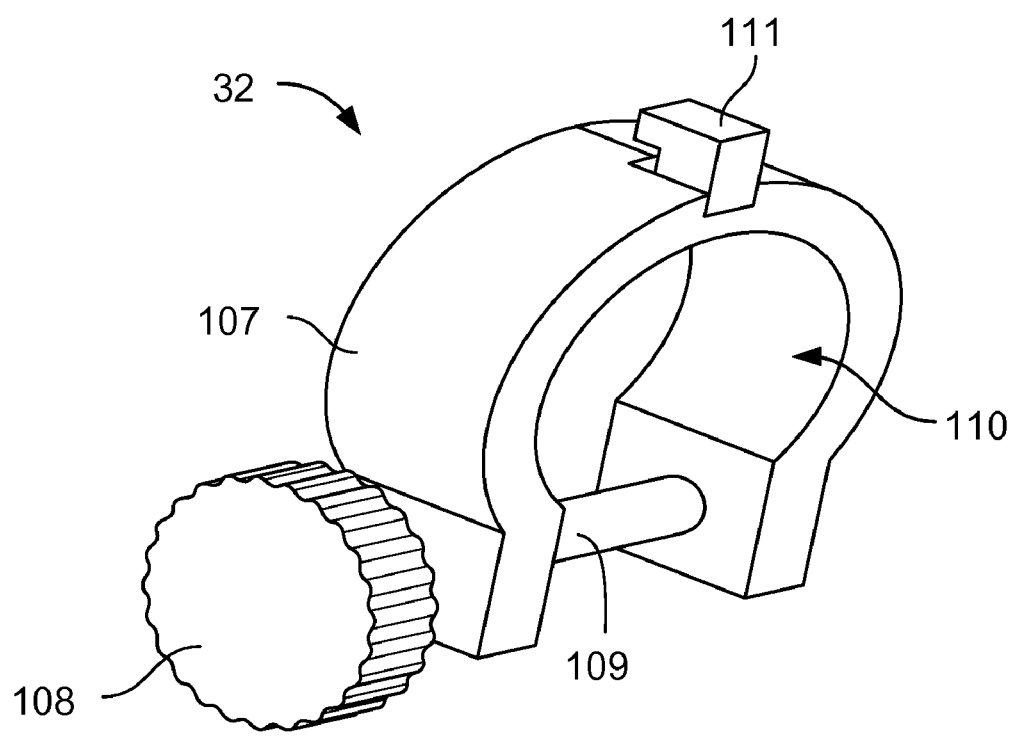
FIG. 15 is an example of a tension slider ring for use in a shoulder lift.

In order for the bent tubular support 35 to attach to the spring clamp 30, the forward flexion attachment 34 is screwed onto the top half 85 of the clamp 30 into the forward flexion attachment slot 86. FIG. 13A shows the forward flexion attachment 34 and the knob 29 that locks the bent tubular support 35 in place inside of the forward flexion attachment. The forward flexion attachment 34 provides a support for the bent tubular support 35 to slide into and rotate within when not locked in place. Turning flexion knob 29 enables the bent tubular support 35 to be locked in place. FIG. 13B shows this forward flexion knob 29 and the mechanism that locks the bent tubular support 35 in place. The forward flexion knob 29 is turned which applies a direct pressure onto the bent tubular shaft 35 at its lower end, thereby locking the bent tubular shaft into place.

The linear spring scale 31 (seen in FIG. 14) enables the surgeon or operating room technician to monitor the change in the amount of traction exerted on a patient's arm by sliding the tension slider ring 32 along the bent tubular shaft 35. The spring scale 31 may have both English units 105 and Metric units 104 of measurement; this may allow the scale to be universally understood by those who prefer one system over the other. In order to change the traction, the tension slider ring 32 (seen in FIG. 15), which is secured to the upper end of the linear spring scale 31, may be pulled upwards along the bent tubular shaft 35 or slid downward along the bent tubular shaft 35 to create the desired tension in the cable 25. The linear spring scale 31 measures the force being applied to the patient's arm via the tension in the cable 25, and provides the surgeon or operating room technician with a quantifiable measure of the traction being applied.

The spring scale 31 connects to tension slider ring 32 by hooking spring scale ring 102 formed on the spring scale 31 to the weight slider hook 111 formed on the tension slider ring 32. In particular, the spring scale ring 102 is placed over the weight slider hook 111 of the tension slider ring 32. If a change in traction is desired, the surgeon or technician loosens the tension slider ring 32 by turning weight slider knob 108 and sliding the weight slider 32 further up the bent tubular shaft 35 if greater force is desired or further down the bent tubular shaft 35 if less three is desired. Once the desired traction is achieved, the weight slider knob 108 can be tightened to lock the tension slider ring 32 in place along the bent tubular shaft 35. By turning the weight slider knob 108, the two opposing sides of the tension slider ring 32 are brought together, thereby tightening the tension slider ring 32 around the bent tubular shaft 35.

In some implementations, a shoulder lift has a lightweight design and no separate parts. In such implementations, the shoulder lift can be stored as an entire unit in an out-of-the-way location. If necessary, the lift can be taken apart, for example, for cleaning, and easily put back together.

As illustrated in FIG. 1, for example, the semi-circular boom design of the shoulder lift 23 may serve to keep the shoulder lift 23 out of the way during surgery. In fact the design may eliminate (or at least reduce) interference by the shoulder lift 23 with the sterile field. For example, the cable 25 is the closest piece of the shoulder lift 23 to the sterile environment, and even it attaches to the arm sleeve 24 and remains outside of the sterilized region. The lift 23 also attaches to the far end of the operating table 20, creating an attachment location outside of the surgical field.

Figure 16A:
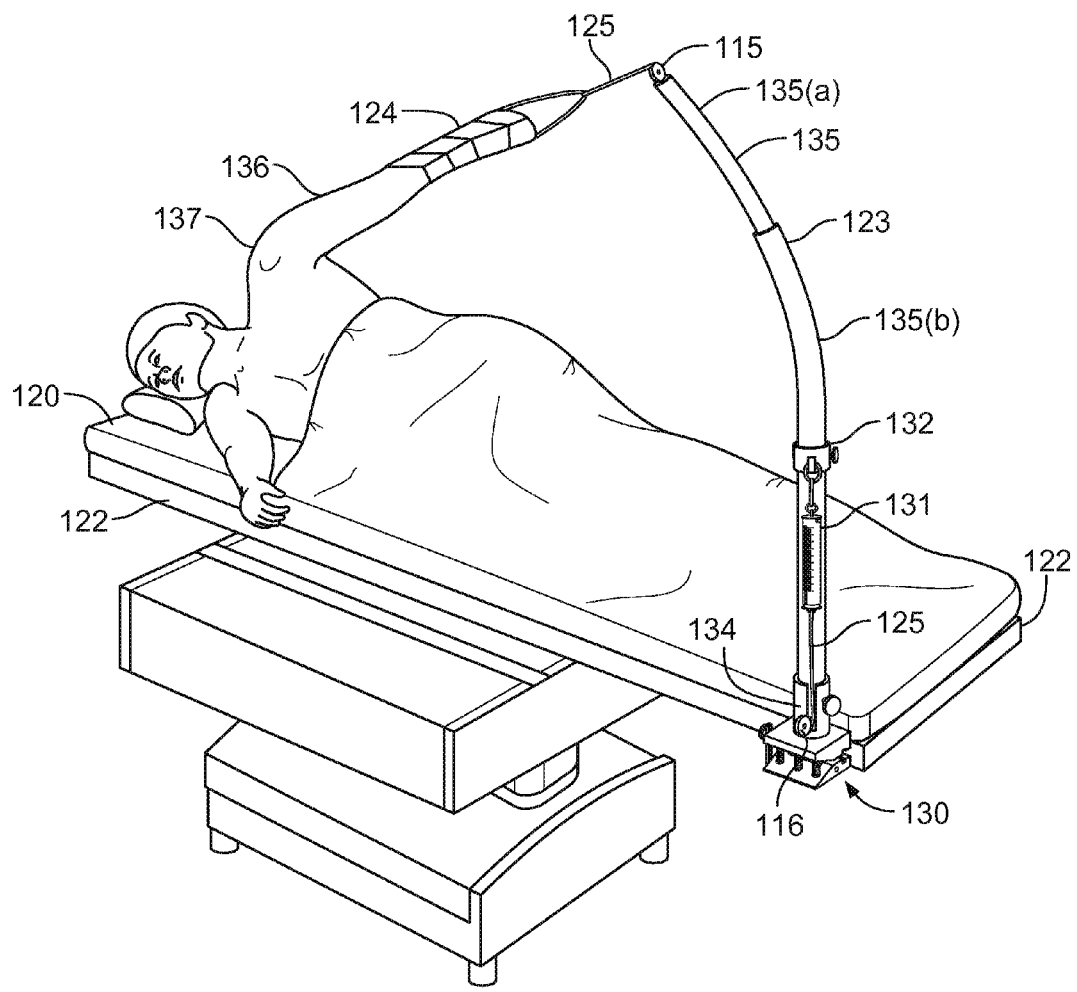
FIGS. 16A and 16B are perspective views of an example of a shoulder lift demonstrating use of the shoulder lift to hold a patient's arm above the patient's body.
Figure 16B:
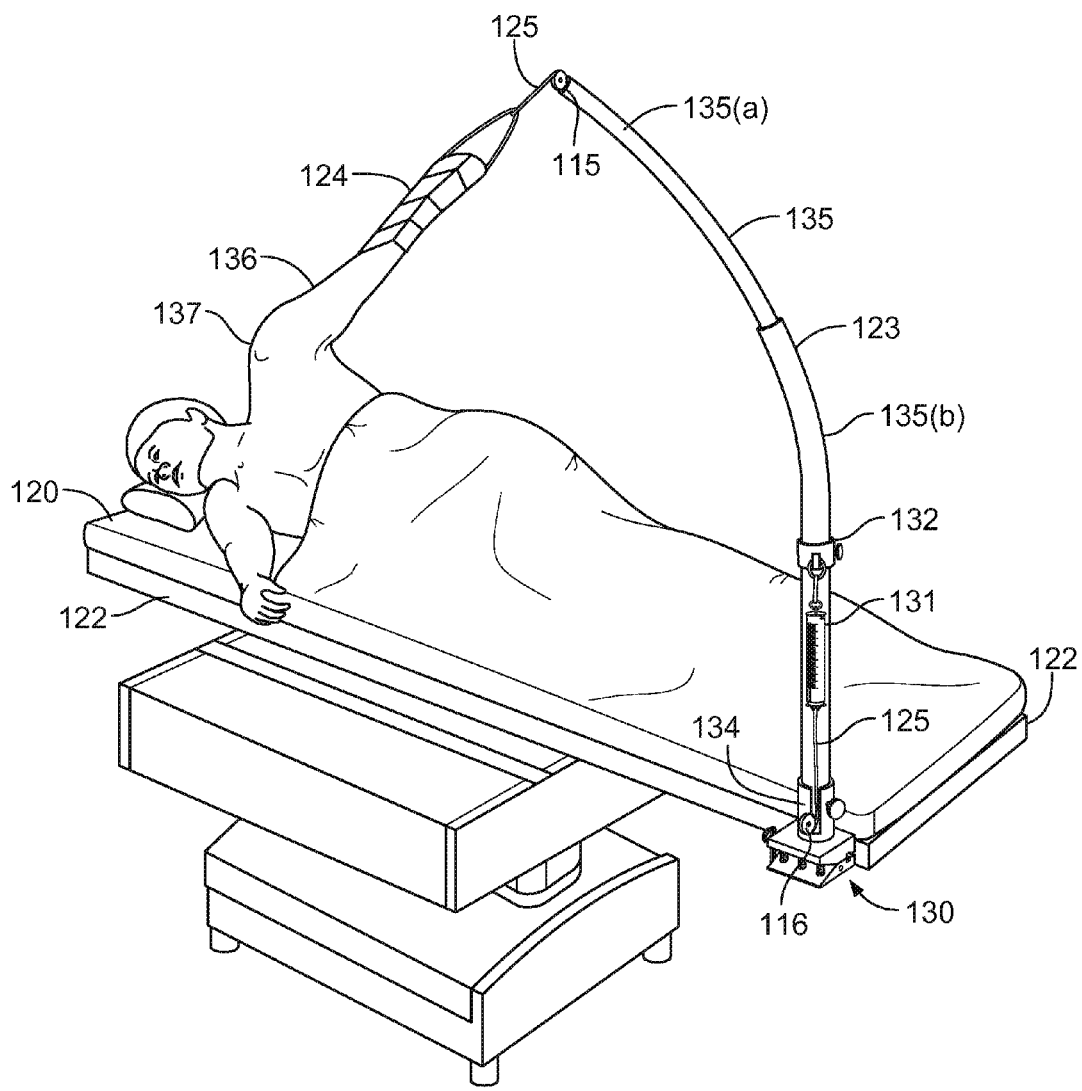
Figure 17:
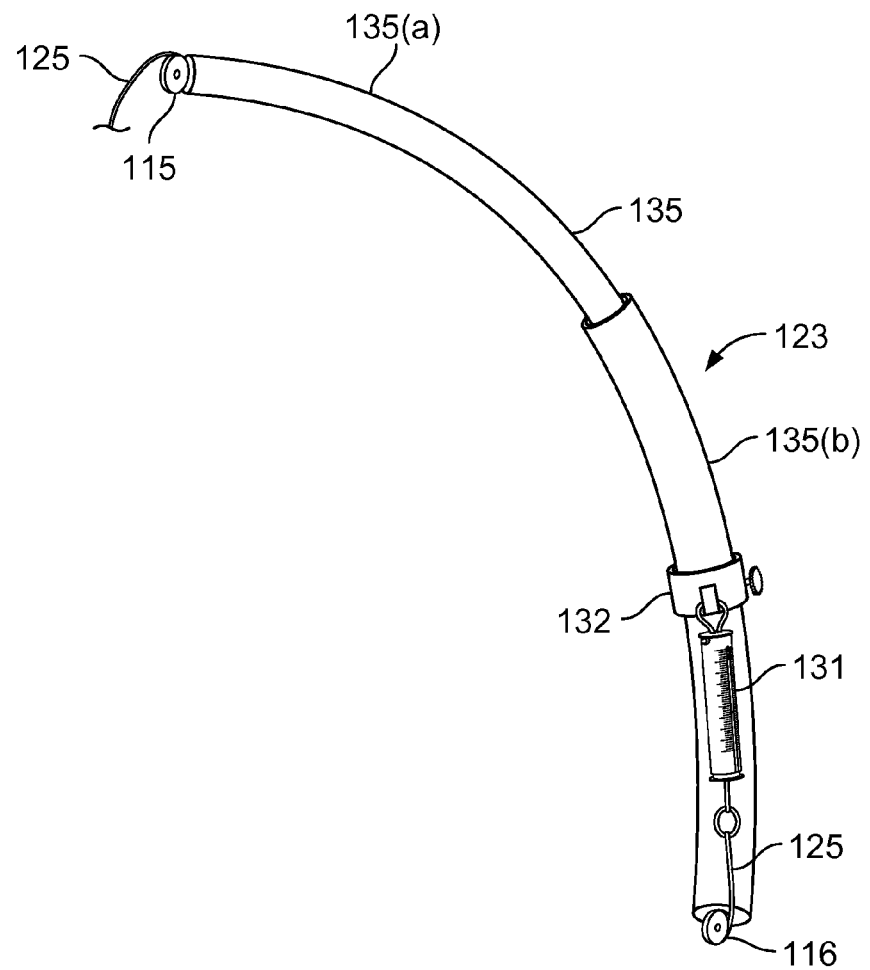
FIG. 17 is a perspective view of the shoulder lift of FIGS. 16A and 16B.

Referring to FIGS. 16A, 16B, and 17, there is shown a second example of a shoulder lift 123 for holding a patient's arm 136 above the patient's body during shoulder surgery. The shoulder lift 123 is attached to the operating table 120 with the patient lying on his/her side during the surgical procedure. The table has two rails 122 on opposite sides to which surgical equipment can be attached and held during surgical procedures. The shoulder lift 123 is attached to one of these rails 122, depending upon on which shoulder 137 the operation is being performed. For example, if the patient's left shoulder is the shoulder on which the operation is being performed, the shoulder lift 123 may be attached to the rail 122 on the patient's ride side. Similarly, if the patient's right shoulder is the shoulder on which the operation is being performed, the shoulder lift 123 may be attached to the rail 122 on the patient's left side.

The shoulder lift 123 includes a system cable 125, a telescoping bent cylindrical shaft 135, first and second pulley systems 115 and 116 over which the system cable 125 runs, a spring clamp 130, a forward flexion attachment 134 that supports the telescoping bent cylindrical shaft 135, a weight slider 132, and a linear spring scale 131.

The telescoping bent cylindrical shaft 135 is formed from an inner bent cylindrical support 135(*a*) and an outer bent cylindrical support 135(*b*), both of which are hollow and both of which are configured to have substantially the same curvature. The inner bent cylindrical support 135(*a*), however, is configured to have a cylindrical circumference that is slightly less than the cylindrical circumference of the outer bent cylindrical support 135(*b*).

The outer bent cylindrical support 135(*b*) is further configured to be able to receive the inner bent cylindrical support 135(*a*) within its interior such that the inner bent cylindrical support 135(*a*) is free to slide in and out (or up and down) within the outer bent cylindrical support 135(*b*). As such, the bent cylindrical shaft 135 may be said to be telescoping in that its length may be adjusted by sliding the inner bent cylindrical support 135(*a*) into or out of the outer bent cylindrical support 135(*b*). For example, comparing FIG. 16A to FIG. 16B reveals that the length of the telescoping bent cylindrical shaft 135 can be adjusted by sliding the inner bent cylindrical support 135(*a*) into and out of the outer bent cylindrical support 135(*b*).

One or both of the inner bent cylindrical support 135(*a*) and the outer bent cylindrical support 135(*b*) may be made from a light weight, strong metal that also withstands corrosion from cleaning agents, such as, for example, aluminum or titanium.

First pulley system 115 is mounted on the end of the inner bent cylindrical support 135(*a*) that is opposite from the end of the inner bent cylindrical support 135(*b*) that is received within the interior of the outer bent cylindrical support 135(*b*) such that the cable 125 can be run over the first pulley system 115 and threaded through the interior of the inner bent cylindrical support 135(*a*). Second pulley system 116 is mounted on the end of the outer bent cylindrical support 135(*b*) that is opposite from the end of the outer bent cylindrical support 135(*b*) that receives the inner bent cylindrical support 135(*a*) such that after running the cable 125 over the first pulley system 115 and through the interior of the inner bent cylindrical support 135(*a*), the cable also can be threaded through the interior of the outer bent cylindrical support 135(*b*) and over the second pulley system 116.

The telescoping bent cylindrical shaft 135 supports an arm 136 through the system cable 125. The arm 136 is wrapped in the arm sleeve 124 which connects to a first end of the system cable 125. The cable 125 runs over the first pulley system 115 and then through the interior of the telescoping bent cylindrical shaft 135 down towards the second pulley system 116. The cable 125 emerges from the interior of the bent cylindrical shaft and runs over the second pulley system 116 and then loops back upward again along the telescoping bent cylindrical shaft 135, where the second end of the cable 125 is attached to one end of the linear spring scale 131. A second end of the linear spring scale 131 is connected to a tension slider ring 132, and the tension slider ring 132 is configured to be able to slide along the telescoping bent cylindrical shaft 135 and to be locked into a desired position along the telescoping bent cylindrical shafts 135. By sliding the tension slider ring 132 up and down the telescoping bent cylindrical shafts 135, the tension in the cable 125 can be adjusted, thereby enabling the traction applied to the patient's arm 136 to be varied. For example, sliding the tension slider ring 132 up the telescoping bent cylindrical shaft 35 increases the tension in the cable 125 thereby reducing the traction applied to the patient's arm 136. Similarly, sliding the tension slider ring 132 down the bent tubular shaft 135 decreases the tension in the cable 125 thereby reducing the traction applied to the patient's arm 136. Meanwhile, the linear spring scale 131 measures the force being exerted on the patient's arm 136 via the tension in the cable 125, thereby providing the surgeon or the operating room technician with a quantifiable measure of the amount of traction being applied to the patient's arm 136.

The shoulder lift 123 is configured to enable the angle of abduction of the patient's arm 136 to be changed by increasing or decreasing the length of the telescoping bent it) cylindrical shaft 135. For example, extending the length of the telescoping bent cylindrical shaft 135 by sliding the inner bent support 135(*a*) further out of the outer bent support 135(*b*) enables the angle of abduction of the patient's arm 136 to be increased. In contrast, decreasing the length of the telescoping bent cylindrical shaft 135 by sliding the inner bent support 135(*a*) further into the outer bent support 135(*b*) enables the angle of abduction of the patient's arm 136 to be decreased.

Various different mechanisms may be employed to fix the length of the telescoping bent cylindrical shaft 135 by locking the inner bent support 135(*a*) in a fixed position relative to the outer bent support 135(*b*). For example, in some implementations, the cylindrical circumference of the inner bent support 135(*a*) may be very nearly the same as but just slightly shorter than the outer bent support 135(*b*). In such implementations, a locking collar may be fit around the outside of the outer bent support 135(*b*) near the end of the outer bent support 135(*b*) that receives the inner bent support 135(*a*), and the locking collar may be configured such that its cylindrical circumference can be increased or decreased. Decreasing the cylindrical circumference of the locking collar increases the force applied by the locking collar on the outer bent support 135(b), which may result in reducing the cylindrical circumference of the outer bent support 135(b) sufficiently to restrict the inner bent support 135(a) from sliding within the interior of the outer bent support 135(b), thereby locking the length of the telescoping bent cylindrical shaft 135. Additionally or alternatively, multiple locking holes may be cut into the side of the outer bent support 135(b), and one or more spring-loaded locking pins may be incorporated into the inner bent support 135(a). In such implementations, the length of the telescoping bent cylindrical shaft 135 may be locked by aligning a spring-loaded locking pin from the inner support 135(a) with a particular one of the locking holes cut into the side of the outer bent support 135(b) such that the spring-loaded locking pin extends through the hole in the outer bent support 135(b) serving to lock the inner bent support 135(a) and the outer bent support 135(b) at a desired length. In an alternative implementation, a quick release handle may be attached to the outer bent support 135(b), and when the desired angle is achieved, the position may be locked by the quick release system.

In some implementations, there may be a possibility of excess cable existing when the shoulder lift 123 is adjusted into different angles of abduction. Consequently, mechanisms for accommodating such excess cable may be employed. For example, a slot may be formed in the outer bent support 135(b) such that the extra cable can be pulled out of the telescoping bent cylindrical support 135 and the cable can be locked at a fixed length. This may enable the tension in the cable to be adjusted accurately, by a threaded rod on the underside of the outer bent support 135(b). The threads may provide accurate readings of the spring deflection and thus accurate readings of the traction on the patient's arm.

Figure 18:
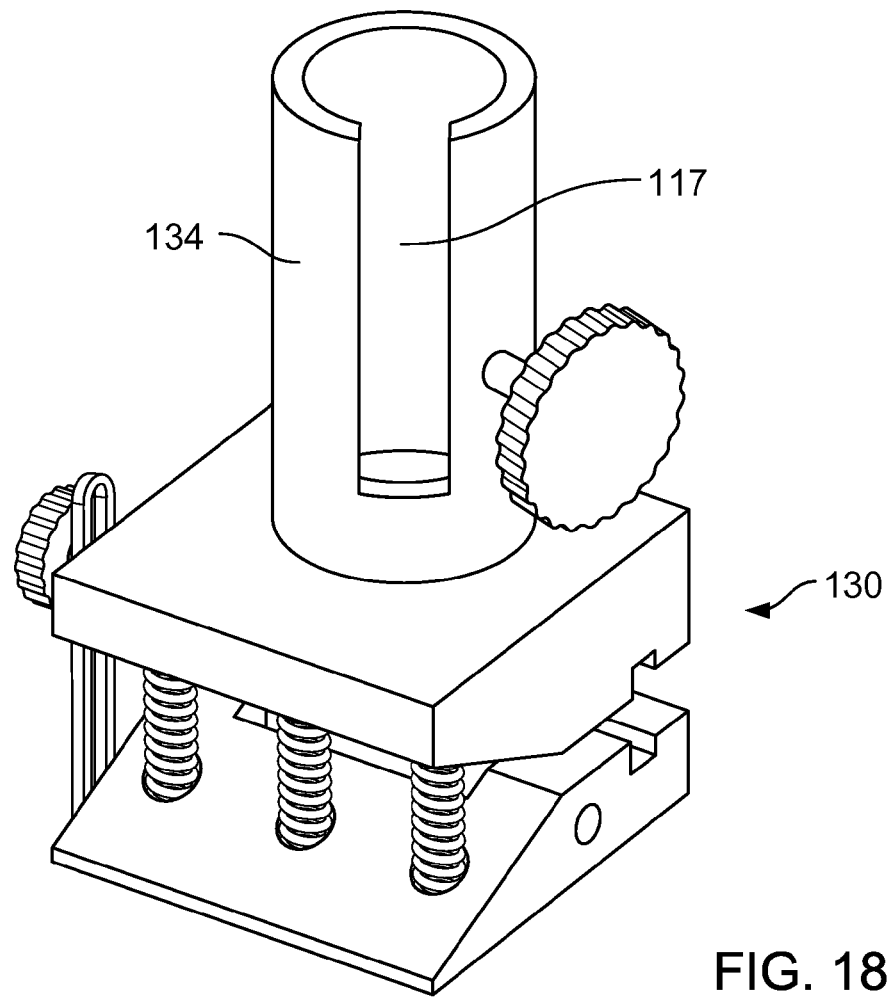
FIG. 18 is a perspective view of an example of a clamp for attaching a shoulder lift to an operating table.

In some implementations, a modified version of the forward flexion attachment 34 illustrated in FIG. 7 may be used to mount the telescoping bent cylindrical shaft 123 to the clamp 130 for attachment to the operating table 120. For example, FIG. 18 illustrates an example of a forward flexion attachment 134 for mounting the telescoping bent cylindrical shaft 123 to clamp 130. As illustrated in FIG. 18, a slot 117 is formed in the forward flexion attachment 134 to accommodate the second pulley system 102 and to enable the cable 125 to exit from the end of the telescoping bent cylindrical shaft 123 for connection to the spring scale 131.

Figure 19:
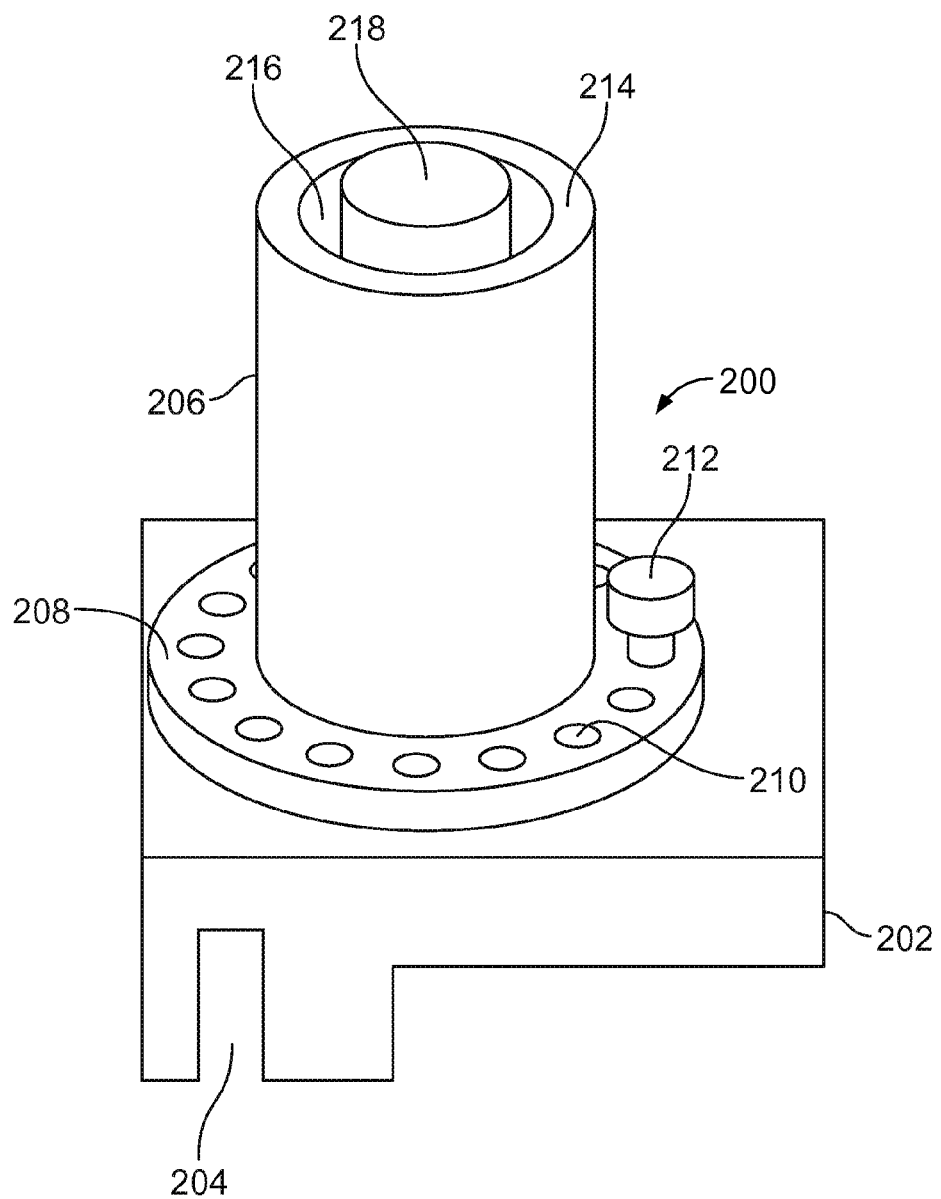
FIG. 19 is a perspective view of an example of a support for attaching a shoulder lift to an operating table.

Other structures also may be employed to attach a shoulder lift, such as, for example, shoulder lift 23 or shoulder lift 123, to an operating table. For example, FIG. 19 is an illustration of one such alternative shoulder lift attachment mechanism 200. As illustrated in FIG. 19, the attachment mechanism 200 includes a mounting plate 202 on the underside of which a single slot 204 is formed that is configured to slide onto the operating table and latch into place.

In addition, a forward flexion attachment 206 is positioned above the mounting plate 202. The forward flexion attachment 206 includes a circular rotation plate 208 that is configured to enable the forward flexion attachment 206 to rotate on the top surface of the mounting plate 202 and through which multiple locking holes 210 are formed. A locking hole (not shown) having substantially the same diameter as the locking holes 210 formed through the rotation plate 208 is formed through the mounting plate 202 in a position such that as the rotation plate 208 is rotated the locking holes 210 formed through the rotation plate 208 overlap the locking hole formed through the mounting plate 202. The rotation plate 208 thus can be locked in place so as to prevent rotation by threading a locking pin 212 through one of the locking holes 210 formed through the rotation plate 208 such that the locking pin 212 also engages the locking hole formed through the mounting plate 202.

The forward flexion attachment 206 also includes a cylindrical boom support column 214 that is coupled (e.g., welded or screwed) to the rotation plate 208. The cylindrical boom support column 214 is hollow and forms an interior opening 216 that is configured to receive the bent shall 218 of the shoulder lift. The dimensions of the interior opening 216 of the cylindrical boom support column 214 may be configured to be very nearly the same size as the bent shaft 218 such that the bent shaft 218 can be secured within the cylindrical boom support column 214 by press-fitting the bent shaft 218 into the boom support column 214. As such, the boom support column 214 holds the bent shaft 218 securely in place, enabling the bent shaft to be attached to an operating table by the shoulder lift attachment mechanism 200. In addition, because the bent shaft 218 is press-fit into the cylindrical boom support column 214, rotating the rotation plate 208 causes both the boom support column 214 and the bent shaft 218 to rotate. Thus, the surgeon or operating room technician can change the forward flexion angle of a patient's arm by rotating the rotation plate 208 of the shoulder lift attachment mechanism 200.

A number of implementations have been described. Nevertheless, it will be understood that various modifications may be made. For example, in some implementations, tension slider ring 32 and/or tension slider ring 132 may be replaced by a fabric strap that is secured to the shoulder lift using hook and loop fasteners. Furthermore, an electronic spring scale may be employed that enables the tension and thus the traction to be changed by pressing buttons. Additionally or alternatively, the angle of abduction slot and the adjustable pulley may be maintained, but the traction system and cable may be internalized within the semi-circular boom. Finally, a descending cable may be added to the end of the semi-circular boom to connect to the arm sling near the patient's shoulder to increase visibility and to help keep the patient's arm in the desired vertical position.

What is claimed is:

1. A surgical shoulder lift comprising:
   a hollow, curved boom having a first end and a second end, the hollow, curved boom defining an interior of the curved boom, a first opening leading to the interior of the curved boom being formed at the first end of the curved boom and a second opening leading to the interior of the curved boom being formed at the second end of the curved boom;
   a first pulley mounted proximately to the first end of the curved boom;
   a second pulley mounted proximately to the second end of the curved boom;
   a mounting assembly configured to latch onto a rail of an operating table and having a hollow columnar support, the hollow columnar support defining an interior of the columnar support that is configured to receive at least a portion of the second end of the curved boom and secure the curved boom within the columnar support;
   a tension slider ring wrapped around at least a portion of the circumference of the curved boom at a position along the curved boom that is between the first and second ends of the curved boom;
   a spring scale having a first end and a second end, the first end of the spring scale being coupled to the tension slider ring; and a cable having a first end and a second end, the cable running over the first pulley, through the first opening formed at the first end of the curved boom and the second opening formed at the second end of the curved boom such that the cable is threaded through the interior of the curved boom, and over the second pulley, the first end of the cable being configured to be coupled to an arm sleeve for holding a patient's arm and the second end of the cable being coupled to the second end of the spring scale, wherein the spring scale is configured to measure the force with which the cable pulls on the second end of the spring scale.

2. The surgical shoulder lift of claim 1 wherein the hollow, curved boom is a semi-circular boom.

3. The surgical shoulder lift of claim 1 wherein the hollow, curved boom has an adjustable length.

4. The surgical shoulder lift of claim 3 wherein the hollow, curved boom comprises:
a hollow, outer curved shaft having a first end and a second end, the hollow, outer curved shaft defining an interior of the hollow, outer curved shaft, a first opening leading to the interior of the outer curved shaft being formed at the first end of the outer curved shaft and a second opening leading to the interior of the outer curved shaft being formed at the second end of the outer curved shaft; and
a hollow, inner curved shaft having a first end and a second end, the hollow, inner curved shaft defining an interior of the hollow, inner curved shaft, a first opening leading to the interior of the inner curved shaft being formed at the first end of the inner curved shaft and a second opening leading to the interior of the inner curved shaft being formed at the second end of the inner curved shaft, wherein:
a circumference of the outer curved shaft is greater than a circumference of the inner curved shaft,
the first opening formed at the first end of the inner curved shaft forms the first opening at the first end of the curved boom,
the second opening formed at the second end of the outer curved shaft forms the second opening at the second end of the curved boom, and
the first opening at the first end of the outer curved shaft is configured to receive the second end of the inner curved shaft such that the length of the curved boom can be adjusted by sliding the inner curved shaft into and out of the outer curved shaft.

5. The surgical shoulder lift of claim 4 further comprising a means for locking the inner curved shall in a fixed position within the outer curved shaft.

6. The surgical shoulder lift of claim 1 wherein the tension slider ring is configured to slide along the curved boom.

7. The surgical shoulder lift of claim 6 wherein the tension slider ring is configured to increase tension in the cable by sliding the tension slider ring along the curved boom away from the second end of the curved boom and toward the first end of the curved boom.

8. The surgical shoulder lift of claim 6 wherein the tension slider ring is configured to decrease tension in the cable by sliding the tension slider ring along the curved boom towards the second end of the curved boom and away from the first end of the curved boom.

9. The surgical shoulder lift of claim 6 further comprising a means for locking the tension slider ring in a fixed position along the curved boom.

10. The surgical shoulder lift of claim 1 wherein the tension slider ring includes a collar configured to be wrapped around at least a portion of the circumference of the curved boom, the collar being formed at least partially from a metal.

11. The surgical shoulder lift of claim 1 wherein the tension slider ring includes a fabric strap having a hook and loop fastening mechanism, the fabric strap being configured to be wrapped around the circumference of the curved boom and fastened to itself using the hook and loop fastening mechanism.

12. The surgical shoulder lift of claim 1 wherein the mounting assembly configured to latch onto a rail of an operating table comprises a clamp configured to clamp onto a rail of an operating table.

13. The surgical shoulder lift of claim 1 wherein the second end of the curved boom is press-fit into the interior of the columnar support of the mounting assembly.

14. The surgical shoulder lift of claim 1 wherein the hollow columnar support of the mounting assembly is configured to enable the curved boom to rotate within the interior of the hollow columnar support.

15. The surgical shoulder lift of claim 14 further comprising a means for locking the curved boom into a fixed position within the interior of the hollow columnar support such that rotation of the curved boom within the interior of the hollow columnar support is prevented.

16. The surgical shoulder lift of claim 1 wherein:
the mounting assembly includes a rotatable plate;
the hollow columnar support is mounted on the rotatable plate such that the hollow columnar support rotates when the rotatable plate rotates; and
the curved boom is secured within the interior of the hollow columnar support such that the curved boom and the hollow columnar support rotate together when the rotatable plate rotates.

17. The surgical shoulder lift of claim 16 further comprising a means for locking the rotatable plate in a fixed position from which rotation is prevented.

18. The surgical shoulder lift of claim 1 wherein the curved boom is formed at least partially from a metal.

19. A surgical shoulder lift comprising:
a hollow, bent shaft having a first end and a second end, the hollow, bent shaft defining an interior of the bent shaft, a first opening leading to the interior of the bent shaft being formed at the first end of the bent shaft and a second opening leading to the interior of the bent shaft being formed at the second end of the bent shaft;
a first pulley mounted proximately to the first end of the bent shaft;
a second pulley mounted proximately to the second end of the bent shaft;
a tension slider ring wrapped around at least a portion of the circumference of the bent shaft at a position along the bent shaft that is between the first and second ends of the bent shaft;
a spring scale having a first end and a second end, the first end of the spring scale being coupled to the tension slider ring; and
a cable having a first end and a second end, the cable running over the first pulley, through the first opening formed at the first end of the bent shaft and the second opening formed at the second end of the bent shaft such that the cable is threaded through the interior of the bent shaft, and over the second pulley, the first end of the cable being configured to be coupled to an arm sleeve for holding a patient's arm and the second end of the cable being coupled to the second end of the spring scale, wherein the spring scale is configured to measure the force with which the cable pulls on the second end of the spring scale.

* * * * *

UNITED STATES PATENT AND TRADEMARK OFFICE
CERTIFICATE OF CORRECTION

PATENT NO. : 8,273,047 B1
APPLICATION NO. : 12/622065
DATED : September 25, 2012
INVENTOR(S) : Brian P. McKeon et al.

Page 1 of 1

It is certified that error appears in the above-identified patent and that said Letters Patent is hereby corrected as shown below:

Cover page, column 1, item (73) (Assignee:), line 6, change "Athletic" to --Athletics--, therefor.

Cover page, column 2, item (57) (Abstract), line 13, change "a to fixed" to --a fixed--, therefor.

Column 13, line 46 (line 2 of claim 5), delete "shall" and insert --shaft--, therefor.

Signed and Sealed this
Twenty-second Day of January, 2013

David J. Kappos
*Director of the United States Patent and Trademark Office*